(12) United States Patent
Cottard et al.

(10) Patent No.: US 7,410,505 B2
(45) Date of Patent: Aug. 12, 2008

(54) COMPOSITION FOR THE OXIDATION DYEING OF KERATIN FIBERS, COMPRISING AT LEAST ONE OXIDATION DYE, AT LEAST ONE ASSOCIATIVE POLYMER, AND AT LEAST ONE AMINOSILICONE

(75) Inventors: François Cottard, Courbevoie (FR); Christine Rondeau, Sartrouville (FR)

(73) Assignee: L'Oreal, S.A., Paris (FR)

( * ) Notice: Subject to any disclaimer, the term of this patent is extended or adjusted under 35 U.S.C. 154(b) by 32 days.

(21) Appl. No.: 10/728,954

(22) Filed: Dec. 8, 2003

(65) Prior Publication Data

US 2004/0163187 A1 Aug. 26, 2004

Related U.S. Application Data

(60) Provisional application No. 60/502,614, filed on Sep. 15, 2003.

(30) Foreign Application Priority Data

Dec. 6, 2002 (FR) .................................. 02 15470

(51) Int. Cl.
*A61K 7/13* (2006.01)
(52) U.S. Cl. ...................... 8/405; 8/406; 8/408; 8/410; 8/411; 8/412; 8/421; 8/515; 8/552; 8/554; 8/555
(58) Field of Classification Search ...................... 8/405, 8/406, 408, 410, 411, 412, 421, 515, 552, 8/554, 555
See application file for complete search history.

(56) References Cited

U.S. PATENT DOCUMENTS

| 6,156,076 | A | 12/2000 | Casperson et al. ............. 8/406 |
| 7,101,405 | B2 | 9/2006 | Cottard et al. |
| 2001/0023515 | A1* | 9/2001 | Cottard et al. ................. 8/406 |
| 2002/0046431 | A1* | 4/2002 | Laurent et al. ................. 8/405 |
| 2003/0140429 | A1* | 7/2003 | Legrand et al. ................ 8/405 |

FOREIGN PATENT DOCUMENTS

| FR | 2 831 807 | 5/2003 |
| WO | WO 00/07550 | 2/2000 |
| WO | WO 00/56285 | 9/2000 |
| WO | WO 01/72271 | 10/2001 |
| WO | WO 02/38116 | 5/2002 |
| WO | WO 02/47632 | 6/2002 |
| WO | WO 01/074273 | 9/2002 |
| WO | WO 02/078661 | 10/2002 |

* cited by examiner

*Primary Examiner*—Eisa B Elhilo
(74) *Attorney, Agent, or Firm*—Finnegan, Henderson, Farabow, Garrett, & Dunner, L.L.P.

(57) ABSTRACT

Disclosed herein is a composition for the oxidation dyeing of keratin fibers, for example of human keratin fibers, such as the hair, containing, in a medium that is suitable for dyeing, a) at least one oxidation dye, b) at least one associative polymer, and c) at least one aminosilicone, wherein the at least one aminosilicone/at least one associative polymer weight ratio is greater than or equal to 1.

74 Claims, No Drawings

COMPOSITION FOR THE OXIDATION DYEING OF KERATIN FIBERS, COMPRISING AT LEAST ONE OXIDATION DYE, AT LEAST ONE ASSOCIATIVE POLYMER, AND AT LEAST ONE AMINOSILICONE

CROSS-REFERENCE TO RELATED APPLICATIONS

This application claims the benefit of U.S. Provisional Application No. 60/502,614, filed on Sep. 15, 2003.

FIELD OF THE INVENTION

Disclosed herein is a composition for the oxidation dyeing of keratin fibers, for example of human keratin fibers, such as hair, comprising at least one oxidation dye, at least one associative polymer and at least one aminosilicone.

BACKGROUND OF THE INVENTION

Dyeing keratin fibers, and for example human hair, with dye compositions containing oxidation dye precursors, generally known as "oxidation bases", for example ortho- or para-phenylenediamines, ortho- or para-aminophenols, and heterocyclic bases is known.

Oxidation dye precursors are compounds that are initially uncolored or only weakly colored, which develop their dyeing power on the hair in the presence of oxidizing agents, leading to the formation of colored compounds. The formation of these colored compounds may result either from an oxidative condensation of the "oxidation bases" with themselves or from an oxidative condensation of the "oxidation bases" with coloration modifiers, or "couplers", which are generally present in the dye compositions used in oxidation dyeing and are can be chosen, for example, from meta-phenylenediamines, meta-aminophenols and meta-diphenols, and certain heterocyclic compounds.

The variety of molecules used, which comprise on one hand "oxidation bases" and on the other hand "couplers", allows a wide range of colors to be obtained.

An oxidative dye composition may generally also comprise at least one cationic polymer which improves the cosmetic properties of the composition. It, however, has been noted that dye compositions comprising these cationic polymers may be unstable, may have unsatisfactory cosmetic properties, and may not remain in the hair after shampooing.

DETAILED DESCRIPTION OF THE INVENTION

However, following substantial research, the present inventors have now found that an oxidation dye composition comprising at least one oxidation dye, at least one associative polymer, and at least one aminosilicone may have at least one advantageous property including good physicochemical stability, as well as good cosmetic properties, for example softness, smoothness, pliability, and lightness.

It has also been found that this composition may provide remanent cosmetic properties with respect to shampoo, that is, it may exhibit good properties associated with resistance to shampooing, also referred to as "good shampoo fastness."

The composition disclosed herein may also make it possible to obtain low selectivity, i.e., few gaps in coloration along the same keratin fiber, which may be differently sensitized (i.e., damaged) between its end and its root.

Thus, disclosed herein is a composition for the oxidation dyeing of keratin fibers, for example of human keratin fibers, such as the hair, comprising, in a medium suitable for dyeing,
a) at least one oxidation dye,
b) at least one associative polymer, and
c) at least one aminosilicone, wherein the weight ratio of the at least one aminosilicone to the at least one associative polymer is greater than or equal to 1.

Also disclosed herein is a ready-to-use composition for the oxidation dyeing of keratin fibers comprising at least one oxidation dye, at least one associative polymer, at least one aminosilicone, wherein the weight ratio of the at least one aminosilicone to the at least one associative polymer is greater than or equal to 1, and at least one oxidizing agent.

As used herein, the expression "ready-to-use composition" means the composition intended for application as it is to the keratin fibers; that is to say, it may be stored as it is before use or may result from the extemporaneous mixing of two or more compositions.

Also disclosed herein is a process for the oxidation dyeing of keratin fibers, and for example of human keratin fibers such as the hair, comprising applying to the fibers a composition (A) comprising, in a medium suitable for dyeing, at least one oxidation dye, at least one associative polymer, and at least one aminosilicone, wherein the weight ratio of the at least one aminosilicone to the at least one associative polymer is greater than or equal to 1, wherein color is developed at alkaline, neutral or acidic pH, by mixing a composition (B) comprising at least one oxidizing agent with the composition (A) at the moment of use or which is applied to the fibers sequentially before or after composition (A), with or without intermediate rinsing.

Further disclosed herein are multi-compartment dyeing devices or multi-compartment kits for the oxidation dyeing of keratin fibers, for example of human keratin fibers such as the hair. A device as disclosed herein may comprise a first compartment comprising at least one oxidation dye, at least one associative polymer, and at least one aminosilicone, wherein the weight ratio of the at least one aminosilicone to the at least one associative polymer is greater than or equal to 1, and a second compartment comprising at least one oxidizing agent.

Other features, aspects, subjects and advantages of the invention will emerge even more clearly on reading the description and the examples that follow.

Aminosilicones

The at least one aminosilicone disclosed herein may be chosen from the aminosilicones referred to in the "International Cosmetic Ingredient Dictionary and Handbook", Ninth Edition 2002" under the names amodimethicone and trimethylsiloxyamadimethicone, the disclosure of which is hereby incorporated by reference.

The at least one aminosilicone may, for example, be chosen from aminosilicones of formulae (I), (II) or (III):

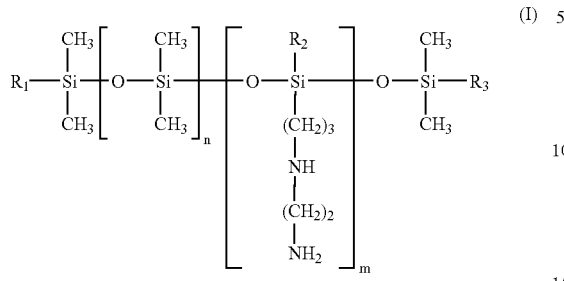

(I)

wherein:
- m and n are numbers such that the sum (n+m) may vary for example from 1 to 1,000, for example from 50 to 250, and as a further example from 100 to 200, it being possible for n to be a number from 0 to 999, for example from 49 to 249, and as a further example from 125 to 175, and for m to be a number from 1 to 1,000, for example from 1 to 10, and as a further example from 1 to 5;
- $R_1$, $R_2$ and $R_3$, which are identical or different, are chosen from a hydroxyl and a $C_1$-$C_4$ alkoxy radical, such as a methoxy radical, wherein at least one of the radicals $R_1$ to $R_3$ is an alkoxy radical.

The hydroxyl/alkoxy molar ratio in formula (I) may range from 0.2:1 to 0.4:1, for example from 0.25:1 to 0.35:1, and as a further example is 0.3:1.

The at least one aminosilicone of formula (I) has a weight-average molecular mass ranging from 2,000 to 1,000,000, and for example ranging from 3,500 to 200,000.

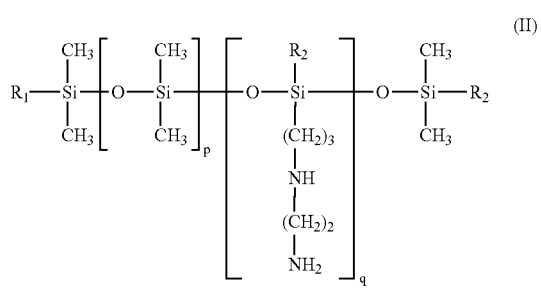

(II)

wherein:
- p and q are numbers such that the sum (p+q) may vary for example from 1 to 1,000, for example from 50 to 350, and as a further example from 150 to 250, it being possible for p to be a number from 0 to 999, for example from 49 to 349, and as a further example from 159 to 239; and for q to be a number from 1 to 1,000, for example from 1 to 10, and as a further example from 1 to 5;
- $R_1$ and $R_2$, which are different, are chosen from a hydroxyl and a $C_1$-$C_4$ alkoxy radical, such as a methoxy radical, wherein at least one of the radicals, $R_1$ or $R_2$, is an alkoxy radical.

The hydroxyl/alkoxy molar ratio may be for example from 1:0.8 to 1:1.1, for example from 1:0.9 to 1:1, and as a further example may be 1:0.95.

The aminosilicone of formula (II) has a weight-average molecular mass ranging, for example, from 2,000 to 200,000, and for example from 5,000 to 100,000, and as a further example from 10,000 to 50,000.

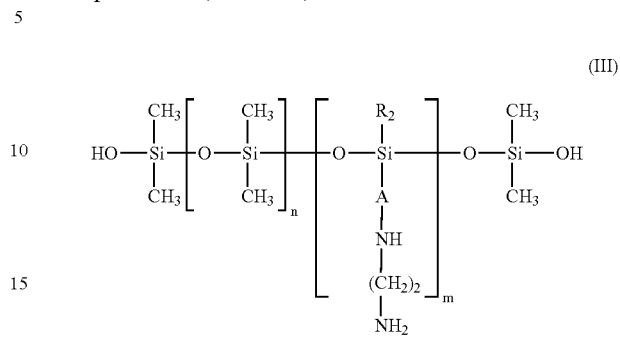

(III)

wherein:
- A is a linear or branched $C_4$-$C_8$ alkyl radical and may be, for example, a $C_4$ alkylene radical,
- m and n are numbers such that the sum (n+m) may vary for example from 1 to 2,000, for example from 50 to 150, it being possible for n to be a number ranging from 0 to 1999, and for example from 49 to 149, and for m to be a number ranging from 1 to 2,000 and for example from 1 to 10.

The viscosity of the at least one aminosilicone of formula (III) may be for example greater than 25,000 mm$^2$/s at 25° C., as a further example may range from 30,000 to 200,000 mm$^2$/s at 25° C., and as a further example ranges from 30,000 to 150,000 mm$^2$/s at 25° C. The viscosity of silicones is measured for example in accordance with the Standard ASTM 445 Appendix C, the disclosure of which is hereby incorporated by reference.

The at least one aminosilicone of formula (III) has a molecular mass ranging, for example, from 2,000 to 1,000,000, and as a further example ranging from 3,500 to 200,000.

The weight-average molecular mass of the at least one aminosilicone is measured by gel permeation chromatography (GPC) at ambient temperature in terms of polystyrene equivalents. The columns used are μ styragel columns. The eluent is THF, the flow rate is 1 ml/min. 200 μl of a 0.5% by weight (on average) solution in THF are injected. Detection is carried out by refractometry and UVmetry.

The commercial product which corresponds to the at least one aminosilicone of formulae (I) to (III) may include in their composition at least one other aminosilicone whose structure is different from formulae (I) to (III).

A product containing at least one aminosilicone of formula (I) is offered by the company Wacker under the name BELSIL ADM 652®.

Products containing at least one aminosilicone of formula (II) are offered by the company Wacker under the name FLUID WR 1300® and BELSIL ADM 6057®.

When these aminosilicones are employed, one embodiment is their use in the form of an oil-in-water emulsion. The oil-in-water emulsion may comprise at least one surfactant. The at least one surfactant may be of any kind, but in one embodiment is, for example, cationic and/or non-ionic. The particles of the at least one aminosilicone in the emulsion may have an average size ranging generally from 3 to 500 nm.

In one embodiment, the at least one aminosilicone of formula (II) may be, for example, a microemulsion with a size ranging from 5 to 60 nm, and for example from 10 to 50 nm. For example, microemulsions of the at least one aminosilicone of formula (II) which are offered under the name FINISH CT 96 E® or SLM 28020® by the company Wacker may be used.

The particles of the at least one aminosilicone of formula (III) in the emulsion have an average size ranging from 5 to 300 nm, for example from 10 to 275 nm, and as a further example from 150 to 275 nm.

At least one aminosilicone of formula (III) is, for example, DC-28299® from the company Corning.

The at least one aminosilicone of formula (I) or (II) may, for example, be chosen so that the contact angle of a hair treated with a composition containing water and 2% AS (active substance) of the at least one aminosilicone ranges from 90 to 180°, and for example from 90 to 130°. In one embodiment, the composition containing the at least one aminosilicone of formula (I) or (II) may be chosen so that the contact angle of the hair treated with the composition ranges from 90 to 180°, and for example from 90 to 130°.

The contact angle measurement is based on the immersion of a hair in distilled water. It comprises evaluating the force exerted by the water on the hair during its immersion in distilled water and during its withdrawal. The forces thus measured are directly related to the contact angle θ between the water and the surface of the hair. The hair is said to be hydrophilic when the angle θ ranges from 0 to 90° and hydrophobic when this angle ranges from 90° to 180°.

The test is performed with locks of natural hair which have been decolored under identical conditions and then washed.

Each lock of 1 g is placed in a crystallizer with a diameter of 75 mm and then covered homogeneously with 5 ml of the test formula. The lock is then left at ambient temperature for 15 minutes and then rinsed for 30 seconds. After being wrung out, the lock is left in the open air until it is completely dry.

For each evaluation, 10 hairs, having undergone the same treatment, are analysed. Each sample, fixed to a precision microbalance, is immersed by its end in a container filled with distilled water. The DCA (dynamic contact angle analyser) balance, from the company Cahn Instruments, allows the force (F) exerted by the water on the hair to be measured.

In parallel the perimeter (P) of the hair is measured via microscopic observation.

The average wettability force on 10 hairs and the section of the hairs analysed make it possible to obtain the contact angle of the hair with water, in accordance with formula:

$$F = P * \lceil lv * \cos \theta$$

wherein F is the wettability force expressed in newtons, P is the perimeter of the hair in meters, ⌈lv is the liquid/water vapour interfacial tension in $J/m^2$ and θ is the contact angle.

The product SLM 28020® from Wacker at a concentration of 12% in water (i.e. 2% of aminosilicone) gives a contact angle of 93° according to the test indicated above.

The at least one aminosilicone of formula (I), (II) or (III) may be present in the composition in an amount ranging from 0.1% to 10%, and for example from 0.5% to 5% by weight, relative to the total weight of the composition.

Associative Polymers

The at least one associative polymer may be a polymer whose molecules are capable, in the formulation medium, of undergoing association with one another or with molecules of other compounds.

In one embodiment, the at least one associative polymer may be an amphiphilic polymer, i.e. a polymer comprising at least one hydrophilic moiety which renders it soluble in water and at least one hydrophobic region (comprising at least one fatty chain) by means of which the polymers interact and undergo assembly with one another or with other molecules.

The at least one associative polymer disclosed herein may be chosen from non-ionic, anionic, cationic and amphoteric associative polymers.

The at least one associative polymer may be chosen from associative polymers comprising at least one fatty chain. The at least one fatty chain comprises, for example, from 8 to 30 carbon atoms, and as a further example from 10 to 30 carbon atoms.

Anionic Associative Polymers

Among the at least one associative polymer comprising at least one fatty chain and of anionic type, mention may be made of:

(I) those comprising at least one hydrophilic unit and at least one fatty-chain allyl ether unit, for example those whose hydrophilic unit may be chosen from an ethylenic unsaturated anionic monomer, a vinylcarboxylic acid, an acrylic acid, a methacrylic acid, and mixtures thereof; wherein the at least one fatty-chain allyl ether unit corresponds to the monomer of formula (IV) below:

$$CH_2=C\ R'CH_2O\ B_nR \qquad (IV)$$

wherein R' is chosen from H and $CH_3$, B is an ethyleneoxy radical, n is chosen from zero and an integer ranging from 1 to 100, R is a hydrocarbon-based radical chosen from alkyl, arylalkyl, aryl, alkylaryl, and cycloalkyl radicals, containing from 8 to 30 carbon atoms, for example from 10 to 24 carbon atoms, and as a further example from 12 to 18 carbon atoms. In one embodiment of a unit of formula (IV), R' is H, n is equal to 10, and R is a stearyl ($C_{18}$) radical.

Anionic amphiphilic polymers of this type are described and prepared, according to an emulsion polymerization process, in patent EP-0 216 479, the disclosure of which is hereby incorporated by reference.

Among these fatty-chain anionic associative polymers those that may be, for example, used are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (IV), and from 0% to 1% by weight of a crosslinking agent which is a well-known copolymerizable unsaturated polyethylenic monomer, for example diallyl phthalate, allyl (meth)acrylate, divinylbenzene, (poly)ethylene glycol dimethacrylate or methylenebisacrylamide.

Among the latter polymers, those that may be, for example, chosen are crosslinked terpolymers of methacrylic acid, of ethyl acrylate, and of polyethylene glycol (10 EO) stearyl ether alcohol (Steareth-10), for example those sold by the company Allied Colloids under the names SALCARE SC 80® and SALCARE SC 90®, which are aqueous 30% emulsions of a crosslinked terpolymer of methacrylic acid, of ethyl acrylate, and of steareth-10 allyl ether (40/50/10).

(II) those comprising at least one hydrophilic unit of unsaturated olefinic carboxylic acid type, and at least one hydrophobic unit of unsaturated carboxylic acid ($C_{10}$-$C_{30}$)alkyl ester type.

For example, these polymers may be chosen from those in which the at least one hydrophilic unit of unsaturated olefinic carboxylic acid type corresponds to the monomer of formula (V) below:

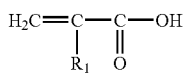

wherein $R_1$ is chosen from H, $CH_3$, and $C_2H_5$, for example acrylic acid, methacrylic acid or ethacrylic acid units, and wherein the at least one hydrophobic unit of unsaturated carboxylic acid ($C_{10}$-$C_{30}$)alkyl ester type corresponds to the monomer of formula (VI) below:

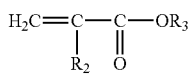

wherein $R_2$ is chosen from H, $CH_3$, and $C_2H_5$, for example, acrylate, methacrylate or ethacrylate units, and as a further example H (acrylate units) or $CH_3$ (methacrylate units), $R_3$ is a $C_{10}$-$C_{30}$, and for example a $C_{12}$-$C_{22}$ alkyl radical.

($C_{10}$-$C_{30}$) alkyl esters of unsaturated carboxylic acids disclosed herein mayinclude, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949, the disclosures of both of which are hereby incorporated by reference.

Among the anionic associative polymers of this type, those that will may be used for example are polymers formed from a monomer mixture comprising:
(i) acrylic acid,
(ii) an ester of formula (VI) described above in which $R_2$ is chosen from H and $CH_3$, $R_3$ is an alkyl radical containing from 12 to 22 carbon atoms, and
(iii) a crosslinking agent, which is a well-known copolymerizable polyethylenic unsaturated monomer, for example diallyl phthalate, allyl (meth)acrylate, divinylbenzene, (poly)ethylene glycol dimethacrylate and methylenebisacrylamide.

Among fatty-chain anionic associative polymers of this type, those that may be used for example are those comprising from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those comprising from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Examples of the above polymers include the products sold by the company Goodrich under the trade names PEMULEN TR1, PEMULEN TR2 and CARBOPOL1382, and for example PEMULEN TR1, and the product sold by the company SEPPIC under the name COATEX SX.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name PERFORMA V 1608 by the company Newphase Technologies.

(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation and being other than (a),
(c) about 0.5% to 60% by weight of a non-ionic monourethane which is the product of reaction of a monohydric surfactant with a monoisocyanate containing monoethylenic unsaturation, such as those described in patent application EP-A-0 173 109, the disclosure of which is hereby incorporated by reference, and for example the terpolymer described in Example 3, namely a methacrylic acid/methyl acrylate/ethoxylated (40 EO) behenyl dimethyl-meta-isopropenylbenzylisocyanate terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

For example, these compounds also comprise as monomer an ester of a carboxylic acid containing α,β-monoethylenic unsaturation and of a $C_1$-$C_4$ alcohol.

An example of a compound of this type which may be mentioned is ACULYN 22 sold by the company Rohm & Haas, which is a methacrylic acid/ethyl acrylate/stearyl methacrylate oxyalkylenated terpolymer.

Non-ionic Associative Polymers

The fatty-chain associative polymers of non-ionic type used herein may be, for example, chosen from:
(1) celluloses modified with groups comprising at least one fatty chain. Examples that may be mentioned include:
  hydroxyethylcelluloses modified with groups comprising at least one fatty chain, such as alkyl, arylalkyl or alkylaryl groups, or mixtures thereof, and wherein the alkyl groups are for example $C_8$-$C_{22}$, such as the product NATROSOL PLUS GRADE 330 CS ($C_{16}$ alkyls) sold by the company Aqualon, or the product BERMOCOLL EHM 100 sold by the company Berol Nobel, and
  those modified with alkylphenyl polyalkylene glycol ether groups, such as the product AMERCELL POLYMER HM-1 500 (nonylphenyl polyethylene glycol (15) ether) sold by the company Amerchol.
(2) hydroxypropylguars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia.
(3) copolymers of vinylpyrrolidone and of fatty-chain hydrophobic monomers. Examples that may be mentioned include:
  the products ANTARON V216 or GANEX V216 (vinylpyrrolidone/hexadecene copolymer) sold by the company I.S.P., and
  the products ANTARON V220 or GANEX V220 (vinylpyrrolidone/eicosene copolymer) sold by the company ISP.
(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name ANTIL 208.
(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton containing at least one fatty chain, such as the PURE THIX compounds sold by the company Sud-Chemie.

In one embodiment, the polyurethane polyethers comprise at least two hydrocarbon-based lipophilic chains having from 6 to 30 carbon atoms, separated by a hydrophilic block, the hydrocarbon-based chains possibly being pendent chains or chains at the end of the hydrophilic block. For example, it is possible for at least one pendent chain to be included. In addition, the polymer may comprise a hydrocarbon-based chain at one end or at both ends of a hydrophilic block.

The polyurethane polyethers may be multiblock, for example in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The non-ionic fatty-chain polyurethane polyethers may be triblock copolymers in which the hydrophilic block is a polyoxyethylenated chain comprising from 50 to 1,000 oxyethylene groups. The non-ionic polyurethane polyethers comprise a urethane linkage between the hydrophilic blocks, hence the name.

By extension, also included among the non-ionic fatty-chain polyurethane polyethers are those in which the hydrophilic blocks are linked to the lipophilic blocks via other chemical bonds.

As examples of non-ionic fatty-chain polyurethane polyethers that may be used, mention may also be made of RHEOLATE 205® containing a urea function, sold by the company Rheox, or the RHEOLATES 208, 204 or 212, and also ACRYSOL RM 184, ACULYN 46 and ACULYN 44 from the company Rohm & Haas (ACULYN 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); ACULYN 44 is a polycondensate of polyethylene glycol containing 150 or 180 mol of ethylene oxide, of decyl alcohol and of methylenebis (4-cyclohexylisocyanate) (SMDI), at 35% by weight in a mixture of propylene glycol (39%) and water (26%)).

Mention may also be made of the product ELFACOS T210 containing a $C_{12-14}$ alkyl chain, and the product ELFACOS T212 containing a $C_{18}$ alkyl chain, from Akzo.

The product DW 1206B from Rohm & Haas containing a $C_{20}$ alkyl chain and a urethane linkage, sold at a solids content of 20% in water, may also be used.

It is also possible to use solutions or dispersions of these polymers, for example in water or in aqueous alcoholic medium. Examples of such polymers that may be mentioned are RHEOLATE 255, RHEOLATE 278 and RHEOLATE 244 sold by the company Rheox. The products DW 1206F and DW 1206J sold by the company Rohm & Haas may also be used. The polyurethane polyethers that may be used herein are for example those described in the article by G. Fonnum, J. Bakke and Fk. Hansen, *Colloid Polym. Sci.*, 271:380-389 (1993), the disclosure of which is hereby incorporated by reference.

Cationic Associative Polymers

The fatty-chain associative polymers of cationic type used herein are chosen, for example, from quaternized cellulose derivatives, polyacrylates containing non-cyclic amine side groups, cationic polyurethanes, cationic polyvinyllactams, and the acrylic terpolymer whose constitution is given below.

The quaternized cellulose derivatives are, for example, quaternized celluloses modified with groups comprising at least one fatty chain, such as alkyl, arylalkyl, and alkylaryl groups containing at least 8 carbon atoms, or mixtures thereof, quaternized hydroxyethylcelluloses modified with groups comprising at least one fatty chain, such as alkyl, arylalkyl, and alkylaryl groups containing at least 8 carbon atoms, or mixtures thereof.

The alkyl radicals borne by the above quaternized celluloses or hydroxyethylcelluloses contain for example from 8 to 30 carbon atoms. The aryl radicals, for example, may be chosen from phenyl, benzyl, naphthyl, and anthryl groups.

Examples of alkylhydroxyethylcelluloses quaternized with $C_8$-$C_{30}$ fatty chains that may be used include quaternized hydroxyethylcelluloses modified with a $C_{12}$ or $C_{18}$ alkyl group, such as the products QUATRISOFT LM 200, QUATRISOFT LM-X 529-18-A, QUATRISOFT LM-X 529-18B ($C_{12}$ alkyl), and QUATRISOFT LM-X 529-8 ($C_{18}$ alkyl) which are sold by the company Amerchol, and the products CRODACEL QM, CRODACEL QL ($C_{12}$ alkyl), and CRODACEL QS ($C_{18}$ alkyl) which are sold by the company Croda.

The polyacrylates containing amine side groups, quaternized or non-quaternized, possess, for example, hydrophobic groups of the steareth 20 type (polyoxyethylenated (20) stearyl alcohol).

Examples that may be mentioned of polyacrylates containing amine side chains include the polymers 8781-121B or 9492-103 provided by the company National Starch.

The cationic associative polyurethanes disclosed herein are chosen, for example, from cationic associative amphiphilic polyurethanes, which are water-soluble or water-dispersible.

The term "water-soluble" or "soluble in water" in relation to the associative polyurethanes signifies that these polymers have a solubility in water at ambient temperature of at least 1% by weight; that is to say that, up to this concentration, no precipitate can be detected by the naked eye and the solution is clear and homogeneous.

Polyurethanes which are "water-dispersible" or "dispersible in water" are polymers which, when suspended in water, spontaneously form droplets having an average size, as measured by light scattering on a Coulter-type apparatus, ranging from 5 nm to 600 nm, and for example ranging from 5 nm to 500 nm.

The family of cationic amphiphilic polyurethanes disclosed herein has been described in French patent application No. 0 009 609, the disclosure of which is hereby incorporated by reference. The family may be represented by the general formula (IA) below:

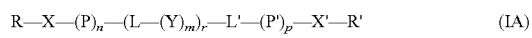

(IA)

wherein:

R and R', which may be identical or different, are chosen from a hydrophobic group and a hydrogen atom;

X and X', which may be identical or different, are chosen from a group comprising an amine function optionally bearing a hydrophobic group, and alternatively the group L";

L, L' and L", which may be identical or different, are a group derived from a diisocyanate;

P and P', which may be identical or different, are a group comprising an amine function optionally bearing a hydrophobic group;

Y is a hydrophilic group;

r is an integer ranging from 1 to 100, for example ranging from 1 to 50, and as a further example from 1 to 25; and n, m and p each are, independently of each other, an integer ranging from 0 to 1000; wherein the molecule comprises at least one protonated or quaternized amine function and at least one hydrophobic group.

In one embodiment of the polyurethanes disclosed herein, the only hydrophobic groups are the groups R and R' at the chain ends.

For example, one family of cationic amphiphilic polyurethanes is the one corresponding to formula (IA) described above and wherein R and R' both independently are a hydrophobic group, X and X' each are a group L", n and p are an integer ranging from 1 to 1000, and L, L', L", P, P', Y and m have the meanings given above.

Another example of a family of cationic amphiphilic polyurethanes is the one corresponding to formula (IA) above wherein R and R' both independently are a hydrophobic group, X and X' each are a group L", n and p are 0, and L, L', L", Y and m have the meanings given above.

The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above in formula (IA) and Q is a leaving group such as a halide, a sulphate, etc.

Yet another example of a family of cationic amphiphilic polyurethanes is the one corresponding to formula (IA) above wherein R and R' both independently are a hydrophobic group, X and X' both independently are a group comprising a quaternary amine, n and p are 0, and L, L', Y and m have the meaning given above in formula (IA).

The number-average molecular mass of the cationic associative polyurethanes ranges, for example, from 400 to 500,000, for example from 1000 to 400,000, and as a further example from 1000 to 300,000.

The expression "hydrophobic group" means a radical or polymer containing a saturated or unsaturated, linear or branched hydrocarbon-based chain, which may comprise at least one heteroatom chosen from P, O, N, and S, or a radical containing a perfluoro or silicone chain. When the hydrophobic group is a hydrocarbon-based radical, it comprises at least 10 carbon atoms, for example from 10 to 30 carbon atoms, as a further example from 12 to 30 carbon atoms, and as a further example from 18 to 30 carbon atoms. In one embodiment, the hydrocarbon-based group is derived from a monofunctional compound.

By way of example, the hydrophobic group may be derived from a fatty alcohol such as stearyl alcohol, dodecyl alcohol or decyl alcohol. It may also be a hydrocarbon-based polymer such as, for example, polybutadiene.

When X and/or X' are a group comprising a tertiary or quaternary amine, X and/or X' may be one of the following formulae:

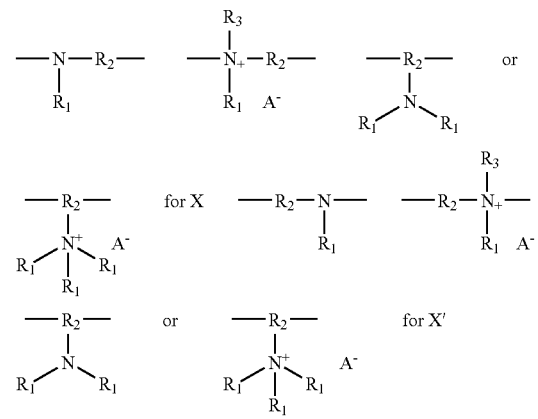

wherein:

$R_2$ is a linear or branched alkylene radical containing from 1 to 20 carbon atoms, optionally comprising a saturated or unsaturated ring, or an arylene radical, at least one of the carbon atoms possibly being replaced with a heteroatom chosen from N, S, O and P;

$R_1$ and $R_3$, which may be identical or different, are chosen from linear and branched $C_1$-$C_{30}$ alkyl and alkenyl radicals, and aryl radicals, at least one of the carbon atoms possibly being replaced with a heteroatom chosen from N, S, O, and P; and $A^-$ is a physiologically acceptable counter-ion.

The groups L, L' and L" of formula (IA) are a group of formula:

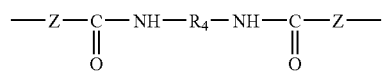

wherein:

Z is chosen from —O—, —S—, and —NH—; and $R_4$ is a linear or branched alkylene radical containing from 1 to 20 carbon atoms, optionally comprising a saturated or unsaturated ring or an arylene radical, at least one of the carbon atoms possibly being replaced with a heteroatom chosen from N, S, O, and P.

The groups P and P' of formula (IA) comprising an amine function may be at least one of the following formulae:

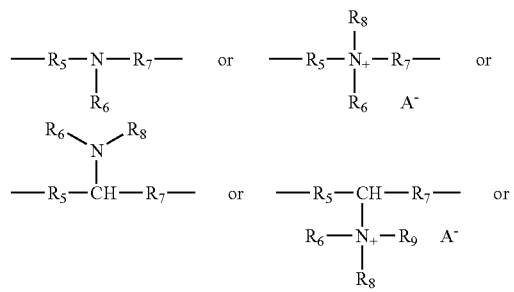

-continued

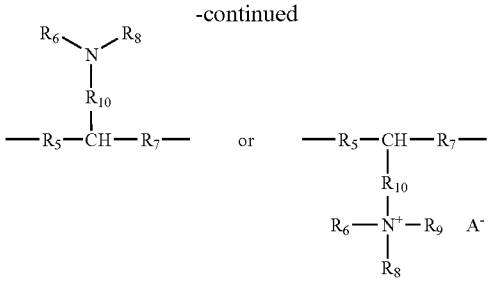

wherein:
- $R_5$ and $R_7$, which are identical or different, are chosen from linear and branched alkylene radicals containing from 1 to 20 carbon atoms, optionally comprising a saturated or unsaturated ring, and from arylene radicals, at least one of the carbon atoms possibly being replaced with a heteroatom chosen from N, S, O and P;
- $R_6$, $R_8$ and $R_9$, which are identical or different, are chosen from linear and branched $C_1$-$C_{30}$ alkyl and alkenyl radicals, and from aryl radicals, at least one of the carbon atoms possibly being replaced with a heteroatom chosen from N, S, O, and P;
- $R_{10}$ is a linear or branched, optionally unsaturated, alkylene group which may contain at least one heteroatom chosen from N, O, S, and P, and
- $A^-$ is a physiologically acceptable counter-ion.

As regards the meaning of Y in formula (IA), the term "hydrophilic group" means a polymeric or non-polymeric water-soluble group.

By way of example, when the hydrophilic group is not a polymer, mention may be made of ethylene glycol, diethylene glycol and propylene glycol.

When the hydrophilic group is a polymer, in accordance with one embodiment, mention may be made, for example, of polyethers, sulphonated polyesters, sulphonated polyamides or a mixture of these polymers. The hydrophilic compound is, for example, a polyether, and as a further example a poly(ethylene oxide) or poly(propylene oxide).

The cationic associative polyurethanes of formula (IA) as used herein are formed from diisocyanates and from various compounds with functions containing labile hydrogen. The functional groups containing labile hydrogen may be alcohol, primary or secondary amines or thiol groups giving, after reaction with the diisocyanate groups, polyurethanes, polyureas and polythioureas, respectively. The term "polyurethanes" as used herein encompasses these three types of polymer, namely polyurethanes per se, polyureas and polythioureas, and also copolymers thereof.

A first type of compound involved in the preparation of the polyurethane of formula (IA) is a compound comprising at least one unit containing an amine function. This compound may be multifunctional, but the compound is, for example, difunctional, that is to say that, according to an embodiment, this compound comprises two labile hydrogen atoms borne, for example, by a hydroxyl, primary amine, secondary amine or thiol functional group. A mixture of multifunctional and difunctional compounds wherein the percentage of multifunctional compounds is low may also be used.

As mentioned above, this compound may comprise more than one unit containing an amine function. For example, it may be a polymer bearing a repetition of the unit containing an amine function.

Compounds of this type may be chosen from the following formulae:

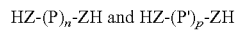

wherein: Z, P, P', n and p are as defined in formula (IA).

Examples of compounds containing an amine function that may be mentioned include N-methyldiethanolamine, N-tert-butyldiethanolamine, and N-sulphoethyldiethanolamine.

The second compound involved in the preparation of the polyurethane of formula (IA) is a diisocyanate corresponding to the formula:

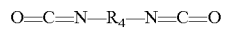

wherein $R_4$ is a linear or branched alkylene radical containing from 1 to 20 carbon atoms, optionally comprising a saturated or unsaturated ring, or an arylene radical, at least one of the carbon atoms possibly being replaced with a heteroatom chosen from N, S, O, and P.

By way of example, mention may be made of methylenediphenyl diisocyanate, methylenecyclohexane diisocyanate, isophorone diisocyanate, toluene diisocyanate, naphthalene diisocyanate, butane diisocyanate, and hexane diisocyanate.

A third compound involved in the preparation of the polyurethane of formula (IA) is a hydrophobic compound intended to form the terminal hydrophobic groups of the polymer of formula (IA).

This compound comprises a hydrophobic group and a functional group containing a labile hydrogen, for example a hydroxyl, primary amine, secondary amine, or thiol function.

By way of example, this compound may be a fatty alcohol such as, for example, stearyl alcohol, dodecyl alcohol, or decyl alcohol. When this compound comprises a polymeric chain, it may be, for example, α-hydroxylated hydrogenated polybutadiene.

The hydrophobic group of the polyurethane of formula (IA) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, wherein R and R' are as defined above in formula (IA) and Q is a leaving group such as a halide, a sulphate, etc.

The cationic associative polyurethane may also comprise a hydrophilic block. This block is provided by a fourth type of compound involved in the preparation of the polymer of formula (IA). This compound may be multifunctional. For example, it may be difunctional. It is also possible to have a mixture in which the percentage of multifunctional compound is low.

The functional groups containing a labile hydrogen are chosen from alcohol, primary amine, secondary amine, and thiol functional groups. This fourth type of compound may be a polymer terminated at the chain ends with one of these functional groups containing a labile hydrogen.

By way of example, when the fourth type of compund is not a polymer, mention may be made of ethylene glycol, diethylene glycol and propylene glycol.

When the fourth type of compound is a hydrophilic polymer, mention may be made, for example, of polyethers, sulphonated polyesters and sulphonated polyamides, or a mixture of these polymers. The hydrophilic compound is chosen from a polyether, a poly(ethylene oxide), and a poly(propylene oxide).

The hydrophilic group termed Y in formula (IA) is optional. Specifically, the units containing a quaternary amine or protonated function may suffice to provide the solubility or water-dispersibility required for this type of polymer in an aqueous solution.

Although the presence of a hydrophilic group Y is optional, cationic associative polyurethanes comprising such a group are, however, used in one embodiment disclosed herein.

The cationic associative polyurethanes may be water-soluble or water-dispersible.

The cationic poly(vinyllactam) polymers comprise:
a) at least one monomer of vinyllactam or alkylvinyllactam type;
b) at least one monomer of str ure (Ib) or (IIb) below:

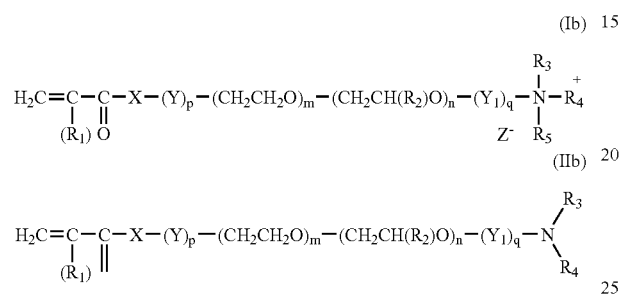

wherein:
X is chosen from an oxygen atom and a radical $NR_6$,
$R_1$ and $R_6$ are, independently of each other, chosen from a hydrogen atom, and linear and branched $C_1$-$C_5$ alkyl radicals,
$R_2$ is a linear or branched $C_1$-$C_4$ alkyl radical,
$R_3$, $R_4$ and $R_5$ are, independently of each other, chosen from a hydrogen atom, linear and branched $C_1$-$C_{30}$ alkyl radicals, and radicals of formula (IIIb):

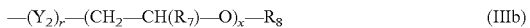

wherein
Y, $Y_1$, and $Y_2$ are, independently of each other, chosen from linear and branched $C_2$-$C_{16}$ alkylene radicals,
$R_7$ is chosen from a hydrogen atom, a linear or branched $C_1$-$C_4$ alkyl radical, and a linear or branched $C_1$-$C_4$ hydroxyalkyl radical,
$R_8$ is chosen from a hydrogen atom and a linear or branched $C_1$-$C_{30}$ alkyl radical,
p, q and r are, independently of each other, either the value zero or the value 1,
m and n are, independently of each other, an integer ranging from 0 to 100,
x is an integer ranging from 1 to 100,
Z is chosen from an organic anion and a mineral acid anion,
with the proviso that:
at least one of the substituents $R_3$, $R_4$, $R_5$ or $R_8$ is a linear or branched $C_9$-$C_{30}$ alkyl radical,
if m or n is other than zero, then q is equal to 1,
if m or n are zero, then p or q is equal to 0.

The cationic poly(vinyllactam) polymers may be crosslinked or non-crosslinked, and may also be block polymers.

In one embodiment, the counter-ion $Z^-$ of the monomers of formula (Ib) is chosen from halide ions, phosphate ions, methosulphate ions, and tosylate ions.

In one embodiment, $R_3$, $R_4$ and $R_5$ are, independently of each other, chosen from a hydrogen atom and a linear or branched $C_1$-$C_{30}$ alkyl radical.

In one embodiment, a monomer (b) is a monomer of formula (Ib) wherein, for example, m and n are zero.

The vinyllactam or alkyvinyllactam monomer is for example a compound of structure (IVb):

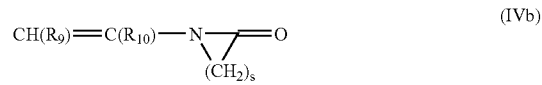

wherein:
s is an integer ranging from 3 to 6,
$R_9$ is chosen from a hydrogen atom and a $C_1$-$C_5$ alkyl radical,
$R_{10}$ is chosen from a hydrogen atom and a $C_1$-$C_5$ alkyl radical,
with the proviso that at least one of the radicals $R_9$ and $R_{10}$ is a hydrogen atom.

For example, the monomer (IVb) may be vinylpyrrolidone.

The cationic poly(vinyllactam) polymers may also contain at least one additional monomer, which is, for example, cationic or non-ionic.

Examples of cationic polymers disclosed herein include the following terpolymers comprising at least:
a)- a monomer of formula (IVb),
b)- a monomer of formula (Ib) in which p=1, q=0, $R_3$ and $R_4$ are, independently of each other, chosen from a hydrogen atom and a $C_1$-$C_5$ alkyl radical, and $R_5$ is a $C_9$-$C_{24}$ alkyl radical, and
c)- a monomer of formula (IIb) in which $R_3$ and $R_4$ are, independently of each other, chosen from a hydrogen atom and a $C_1$-$C_5$ alkyl radical.

In one embodiment, terpolymers comprising, on a weight basis, 40% to 95% of monomer (a), 0.1% to 55% of monomer (c) and 0.25% to 50% of monomer (b) may be used.

Such polymers are described in patent application WO 00/68282, the content of which is hereby incorporated by reference.

Cationic poly(vinyllactam) polymers that may be used include vinylpyrrolidone/dimethylaminopropylmethacrylamide/-dodecyldimethylmethacrylamidopropylammonium tosylate terpolymers, vinylpyrrolidone/dimethylaminopropylmethacrylamide/cocoyldimethylmethacrylamidopropylammonium tosylate terpolymers and vinylpyrrolidone/dimethylaminopropylmethacrylamide/lauryldimethylmethacrylamido-propylammonium tosylate or chloride terpolymers.

The weight-average molecular mass of the cationic poly(vinyllactam) polymers ranges from 500 to 20,000,000, for example from 200,000 to 2,000,000, and as a further example from 400,000 to 800,000.

Among the cationic amphiphilic polymers, mention may also be made of acrylic terpolymers as described in patent application EP-1 090 623, the disclosure of which is hereby incorporated by reference, and which comprises:
from 5% to 80% by weight, for example from 15% to 70% by weight, and as a further example from 40% to 70% by weight of an acrylate monomer (a) chosen from a $C_1$-$C_6$ alkyl acrylate and a $C_1$-$C_6$ alkyl methacrylate;
from 5% to 80% by weight, for example from 10% to 70% by weight, and as a further example from 20% to 60% by weight, of a monomer (b) chosen from a heterocyclic vinyl compound containing at least one nitrogen or sulphur atom, a (meth)acrylamide, a mono- or di($C_1$-$C_4$)

alkylamino($C_1$-$C_4$)alkyl (meth)acrylate and a mono- or di($C_1$-$C_4$)alkylamino($C_1$-$C_4$)alkyl(meth)acrylamide; and from 0.1% to 30% by weight, for example from 0.1% to 10% by weight, of a monomer (c) chosen from:
(i) a urethane produced by reaction between a monoethylenic unsaturated isocyanate and a non-ionic surfactant with a $C_{1-4}$ alkoxy end;
(ii) a block copolymer of 1,2-butylene oxide and of 1,2-ethylene oxide;
(iii) a copolymerizable ethylenic unsaturated surfactant monomer obtained by condensation of a non-ionic surfactant with an α,β-ethylenic unsaturated carboxylic acid or its anhydride;
(iv) a surfactant monomer chosen from the products of reaction such as a urea of a monoethylenic unsaturated monoisocyanate with a non-ionic surfactant containing an amine function;
(v) a (meth)allyl ether of formula $CH_2$=$CR_1CH_2OA_mB_nA_pR_2$ wherein $R_1$ is chosen from a hydrogen atom and a methyl group, A is chosen from a propylenoxy and a butylenoxy group, B is an ethylenoxy, n is chosen from zero and an integer less than or equal to 200, for example less than 100, m and p are chosen from zero and an integer less than n, and $R_2$ is a hydrophobic group of at least 8 carbon atoms, for example of $C_8$-$C_{30}$; and
(vi) a non-ionic monomer of urethane type produced by reaction of a monohydric non-ionic surfactant with a monoethylenic unsaturated isocyanate.

The weight percentages of monomers is based on the total weight of the monomers constituting the terpolymer.

Acrylate monomers (a) that may be used, for example, comprise $C_2$-$C_6$ alkyl acrylates, such as ethyl acrylate.

Examples of monomers (b) which may be mentioned are N,N-dimethylaminoethyl methacrylate (DMAEMA), N,N-diethylaminoethyl acrylate, N,N-diethyl-aminoethyl methacrylate, N-t-butylaminoethyl acrylate, N-t-butylaminoethyl methacrylate, N,N-dimethylamino-propylacrylamide, N,N-dimethylaminopropylmethacrylamide, N,N-diethylamino-propylacrylamide and N,N-diethylaminopropylmethacrylamide. N,N-dimethylaminoethyl methacrylate may be used, for example.

Examples of monomers (c) are the copolymerizable ethylenic unsaturated surfactant monomers obtained by condensing a non-ionic surfactant with an α,β-ethylenic unsaturated carboxylic acid or its anhydride, for example $C_3$-$C_4$ mono- or dicarboxylic acids or their anhydrides, and as a further example acrylic acid, methacrylic acid, crotonic acid, maleic acid, maleic anhydride, and as an additional example itaconic acid and itaconic anhydride.

The monomers (c) that may be used correspond to the copolymerizable ethylenic unsaturated surfactant monomers obtained by condensing a non-ionic surfactant with itaconic acid. Among the non-ionic surfactants which may be mentioned for example are $C_{10}$-$C_{30}$ fatty alcohols alkoxylated with 2 to 100 mol, and for example from 5 to 50 mol of an alkylene oxide, such as, for example, polyethylene glycol ethers of $C_{10}$-$C_{30}$ fatty alcohols, and as a further example the polyethylene glycol ethers of cetyl alcohol which are called CETETH in the CTFA dictionary, 7th edition, 1997, the disclosure of which is hereby incorporated by reference.

Acrylic terpolymers may thus be chosen from acrylic terpolymers comprising acrylates, amino (meth)acrylates and $C_{10}$-$C_{30}$ alkyl itaconate, polyoxyethylenated with 20 mol of ethylene oxide.

Conventional methods for preparing these acrylic terpolymers are known to those skilled in the art. Such methods include solution polymerization, precipitation polymerization, and emulsion polymerization. Terpolymers as disclosed herein and methods for preparing them are described for example in patent applications EP-A-0 824 914 and EP-A-0 825 200, the disclosures of which are hereby incorporated by reference.

Among these terpolymers, embodiments, for example, may use the STRUCTURE® PLUS polymer sold by the company National Starch, which comprises acrylates, amino (meth)acrylates, and $C_{10}$-$C_{30}$ alkyl itaconate, polyoxyethylenated with 20 mol of ethylene oxide, in the form of an aqueous dispersion containing 20% active material.

In addition to these monomers, the terpolymers can contain other monomers which allow the terpolymers to be crosslinked. These monomers are used in relatively low proportions of up to 2% by weight relative to the total weight of the monomers used to prepare the terpolymers. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Crosslinking monomers may be, for example, divinylbenzenes, trivinylbenzenes, 1,2,4-trivinylcyclohexene, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, triallyl pentaerythritols, octaallyl sucroses, cycloparaffins, cycloolefins and N-methylenebisacrylamide.

Amphoteric Associative Polymers

The at least one associative polymer disclosed herein may also be chosen from amphoteric associative polymers.

The term "amphoteric polymers" generally refers to polymers which comprise units K and M randomly distributed in the polymer chain, where K is a unit derived from a monomer comprising at least one basic nitrogen atom and M is a unit deriving from an acidic monomer containing at least one carboxylic or sulphonic groups, or else K and M may be groups deriving from zwitterionic carboxybetaine or sulphobetaine monomers.

K and M may also be a cationic polymer chain containing primary, secondary, tertiary or quaternary amine groups, wherein at least one of the amine groups bears a carboxylic or sulphonic group linked via a hydrocarbon-based radical, or else K and M form part of a chain of a polymer containing an α,β-dicarboxylic ethylene unit in which one of the carboxylic groups has been made to react with a polyamine containing at least one primary or secondary amine groups.

The amphoteric polymers used herein further comprise at least one fatty chain having 8 to 30 carbon atoms, and may be chosen, for example, from polymers derived from polyaspartic acid and containing at least one fatty chain having 8 to 30 carbon atoms, such as those described and prepared in patent application EP 0 767 191, the content of which is incorporated by reference. Such polymers may be prepared in a conventional manner by reacting polysuccinimide (PSI) with fatty-chain ($C_8$-$C_{24}$) amines in a solvent medium in the presence or absence of a basic catalyst such as, for example, aliphatic tertiary amines, followed by amphoterization of the resultant product by reaction with a halogenated organic acid.

Among the $C_8$-$C_{24}$ fatty-chain amines which are reacted with the PSI, mention may be made for example of octylamine, nonylamine, decylamine, dodecylamine, tetradecylamine, hexadecylamine, octadecylamine, octadecenylamine, eicosyldecylamine, octynylamine, decenylamine, dodecenylamine, tetradecenylamine, hexadecenylamine, octadecenylamine and eicosenylamine.

Examples of such polymers are prepared by reacting PSI with n-laurylamine or with n-stearylamine in the presence of N,N-dimethyl-1,3-propanediamine as basic catalyst, followed by amphoterization of the resultant product by reaction with potassium monochloroacetate. These polymers are prepared with greater details on pages 13 to 20 (lines 1-4) and in Examples 1 to 5 on pages 28 to 34 (lines 1-4) of patent application EP0767 191.

The amphoteric polymers derived from polyaspartic acid and containing at least one fatty chain having 8 to 30 carbon atoms may also be chosen from those described and prepared in patent application EP 0 884 344, whose content is incorporated by reference. Polymers of this kind are prepared by reacting gaseous ammonia with a $C_8$-$C_{24}$ alkyl or alkenyl monomaleate in a solvent medium under reduced pressure at a temperature of 120-140° C. for from 4 to 6 hours.

The $C_8$-$C_{24}$ alkyl or alkenyl radicals may for example be chosen from the following linear or branched radicals: decyl, dodecyl, tetradecyl, hexadecyl, octadecyl, and oleyl.

Examples of such polymers include polymers containing aspartic acid units and decyl aspartate units, polymers containing aspartic acid units and dodecyl aspartate units, polymers containing aspartic acid units and cetyl aspartate units, polymers containing aspartic acid units and stearyl aspartate units, and polymers containing aspartic acid units and n-decylaspartamide units, which are described in Examples 1 to 6 in patent application EP 0 884 344.

The amphoteric polymers derived from polyaspartic acid and containing at least one fatty chain having 8 to 30 carbon atoms may also be chosen from those described and prepared in patent application EP 0 959 094, the content of which is incorporated by reference. Polymers of this kind are prepared by reacting, in a solvent medium, gaseous ammonia with a maleic acid monoamide, polyoxyalkylenated and hydrophobically modified by a linear or branched $C_8$-$C_{30}$ alkyl or alkenyl chain, optionally in a mixture with a monoester of maleic acid.

An example of a polymer thus prepared is described in Example 2 on page 11 of patent application EP 0 959 094.

The amphoteric polymers derived from polyaspartic acid and containing at least one fatty chain having 8 to 30 carbon atoms may also be chosen from those described and prepared in patent application EP 0 959 090, the content of which is incorporated by reference. Hydrophobically modified polymers of this kind of high molecular weight are obtained from derivatives of maleic acid and gaseous ammonia and difunctional or polyfunctional amines or alcohols.

Examples of copolymers containing aspartic acid units and cetyl aspartate units or containing aspartic acid units and cetyl aspartate units are given, respectively, in Examples 3 and 5 of patent application EP 0 959 090.

The amphoteric polymers derived from polyaspartic acid and containing at least one fatty chain having 8 to 30 carbon atoms may also be chosen from those described and prepared in patent application EP 0 959 091, the content of which is incorporated by reference. Hydrophobically modified polymers of this kind are prepared from maleic acid monoester or monoamide and gaseous ammonia.

Examples of such copolymers are given in Examples 1, 2, 3 and 5 of patent application EP 0 959 091.

For example, the amphoteric polymers containing at least one fatty chain having 8 to 30 carbon atoms may be chosen from those comprising at least one non-cyclic cationic unit. For example, the amphoteric polymers that may be used may be those prepared from or containing from 1 to 20 mol % of monomer comprising a fatty chain, for example from 1.5 to 15 mol %, and as a further example from 1.5 to 6 mol %, relative to the total number of moles of monomers.

The fatty-chain amphoteric polymers that may be used herein comprise, or are prepared by copolymerizing:
1) at least one monomer of formula (VII) or (VIII):

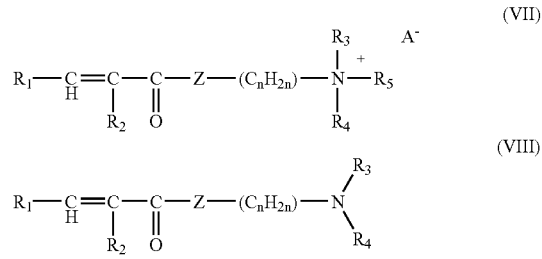

wherein
$R_1$ and $R_2$, which may be identical or different, are chosen from a hydrogen atom and a methyl radical,
$R_3$, $R_4$ and $R_5$, which may be identical or different, are chosen from linear and branched alkyl radicals containing from 1 to 30 carbon atoms,
Z is chosen from an NH group and an oxygen atom,
n is an integer from 2 to 5, and
$A^-$ is an anion derived from an organic or mineral acid, such as a methosulphate anion or a halide such as chloride or bromide;
2) at least one monomer of formula (IX)

$$R_6\text{---}CH\text{=}CR_7\text{---}COOH \qquad (IX)$$

wherein $R_6$ and $R_7$, which may be identical or different, are chosen from a hydrogen atom and a methyl radical; and
3) at least one monomer of formula (X):

$$R_6\text{---}CH\text{=}CR_7\text{---}COX\ R_8 \qquad (X)$$

wherein
$R_6$ and $R_7$, which may be identical or different, are chosen from a hydrogen atom and a methyl radical,
X is chosen from an oxygen and a nitrogen atom, and
$R_8$ is a linear or branched alkyl radical containing from 1 to 30 carbon atoms;
at least one of the monomers of formula (VII), (VIII) or (IX) comprising at least one fatty chain.

The monomers of formulae (VII) and (VIII) are, for example, chosen from dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, and dimethylaminopropylacrylamide, these monomers optionally being quaternized, for example with a $C_1$-$C_4$ alkyl halide or a $C_1$-$C_4$ dialkyl sulphate.

For example, the monomer of formula (VII) is chosen from acrylamidopropyltrimethylammonium chloride and methacrylamidopropyltrimethylammonium chloride.

The monomer of formula (IX) may be, for example, chosen from acrylic acid, methacrylic acid, crotonic acid and 2-methylcrotonic acid. In one embodiment, the monomer of formula (IX) is acrylic acid.

The monomers of formula (X) may be, for example, chosen from $C_{12}$-$C_{22}$, and for example $C_{16}$-$C_{18}$ alkyl acrylates or methacrylates.

The monomers constituting the fatty-chain amphoteric polymers may be, for example, already neutralized and/or quaternized.

The ratio of the number of cationic charges/anionic charges may be, for example, equal to about 1.

The fatty-chain amphoteric polymers disclosed herein comprise, for example, from 1 mol % to 10 mol % of the monomer comprising a fatty chain (monomer of formula (VII), (VIII) or (IX)), and as a further example from 1.5 mol % to 6 mol %.

The weight-average molecular weights of the fatty-chain amphoteric polymers may range from 500 to 50,000,000, and for example range from 10,000 to 5,000,000.

The fatty-chain amphoteric polymers may also contain other monomers such as non-ionic monomers and for example such as $C_1$-$C_4$ alkyl acrylates or methacrylates.

Fatty-chain amphoteric polymers as disclosed herein are described and prepared, for example, in patent application WO 98/44012, the disclosure of which is hereby incorporated by reference.

Among the fatty-chain amphoteric polymers, the ones that may be used are acrylic acid/(meth)acrylamidopropyltrimethylammonium chloride/stearyl methacrylate terpolymers.

In one embodiment, in the oxidation dyeing composition disclosed herein, an associative cationic polymer is used.

The ratio by weight of the at least one aminosilicone to the at least one associative polymer is greater than or equal to 1, for example ranging from 1 to 10, and as a further example from 1 to 5.

Oxidation Dyes

The oxidation dyes that may be used in the compositions disclosed herein are chosen from oxidation bases and/or couplers.

The compositions may, for example, contain at least one oxidation base.

The at least one oxidation base that may be used is chosen from those conventionally used in oxidation dyeing, and among which mention may be made, for example, of orthoand para-phenylenediamines, double bases, ortho- and paraaminophenols, heterocyclic bases, and also the acid addition salts thereof.

Mention may be made, for example, of:

(I) the para-phenylenediamines of formula (XI) below, and the acid addition salts thereof:

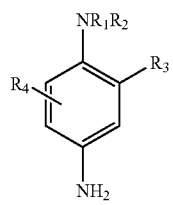

(XI)

wherein:

$R_1$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, and a $C_1$-$C_4$ alkyl radical substituted with a nitrogenous, phenyl, or 4'-aminophenyl group;

$R_2$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical, and a $C_1$-$C_4$ alkyl radical substituted with a nitrogenous group;

$R_1$ and $R_2$ may also form, with the nitrogen atom that bears them, a 5- or 6-membered nitrogen heterocycle optionally substituted with at least one group chosen from alkyl, hydroxyl and ureido groups;

$R_3$ is chosen from a hydrogen atom, a halogen atom such as a chlorine atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, an acetylamino($C_1$-$C_4$) alkoxy radical, a mesylamino($C_1$-$C_4$)alkoxy radical, and a carbamoylamino($C_1$-$C_4$)alkoxy radical, and $R_4$ is chosen from a hydrogen atom, a halogen atom, and a $C_1$-$C_4$ alkyl radical.

Among the nitrogenous groups of formula (XI) above, mention may be made, for example of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium, and ammonium radicals.

Among the para-phenylenediamines of formula (XI) above, mention may be made, for example of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-N,N-bis(β-hydroxyethyl)-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine, and the acid addition salts thereof.

Among the para-phenylenediamines of formula (XI) above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid, may, for example, be used.

(II) As used herein, the term "double bases" means compounds comprising at least two aromatic nuclei bearing amino and/or hydroxyl groups.

Among the double bases that can be used as oxidation bases in the dye compositions disclosed herein, mention may be made, for example of the compounds corresponding to formula (XII) below, and the acid addition salts thereof:

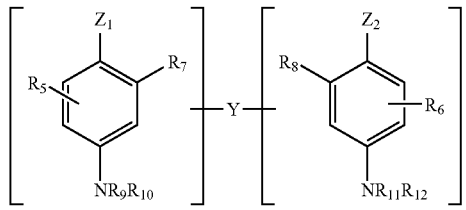

wherein:
- $Z_1$ and $Z_2$, which may be identical or different, are chosen from a hydroxyl and a —$NH_2$ radical which may be substituted with at least one entity chosen from a $C_1$-$C_4$ alkyl radical and a linker arm Y;
- the linker arm Y is a linear or branched alkylene chain containing from 1 to 14 carbon atoms, which may be interrupted by or terminated with at least one entity chosen from a nitrogenous group and at least one heteroatom such as oxygen, sulphur or nitrogen atoms, and optionally substituted with at least one radical chosen from hydroxyl and $C_1$-$C_6$ alkoxy radicals;
- $R_5$ and $R_6$, which may be identical or different, are chosen from a hydrogen atom, a halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, and a linker arm Y; and
- $R_7$, $R_8$, $R_9$, $R_{10}$, $R_{11}$ and $R_{12}$, which may be identical or different, are chosen from a hydrogen atom, a linker arm Y, and a $C_1$-$C_4$ alkyl radical;

wherein the compound of formula (XII) contains only one linker arm Y per molecule.

Among the nitrogenous groups of formula (XII) above, mention may, for example, be made of amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formula (XII) above, mention may be made, for example of N,N'-bis-(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis (β-hydroxyethyl)-N,N'-bis-(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,5-dioxaoctane, and the acid addition salts thereof.

Among these double bases of formula (XII), N,N'-bis(β-hydroxyethyl)-N,N'-bis(4'-aminophenyl)-1,3-diaminopropanol and 1,8-bis(2,5-diaminophenoxy)-3,5-dioxaoctane, or an acid addition salt thereof, may, for example, be used.

(III) the para-aminophenols corresponding to formula (XIII) below, and the acid addition salts thereof:

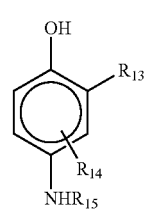

wherein:
- $R_{13}$ is chosen from a hydrogen atom, a halogen atom such as fluorine, a $C_1$-$C_4$ alkyl, a $C_1$-$C_4$ monohydroxyalkyl, a ($C_1$-$C_4$)alkoxy($C_1$-$C_4$)alkyl, a $C_1$-$C_4$ aminoalkyl, and a hydroxy($C_1$-$C_4$)alkylamino($C_1$-$C_4$)alkyl radical;
- $R_{14}$ is chosen from a hydrogen atom, a halogen atom such as fluorine, a $C_1$-$C_4$ alkyl, a $C_1$-$C_4$ monohydroxyalkyl, a $C_2$-$C_4$ polyhydroxyalkyl, a $C_1$-$C_4$ aminoalkyl, a $C_1$-$C_4$ cyanoalkyl, and a ($C_1$-$C_4$)alkoxy-($C_1$-$C_4$)alkyl radical; and
- $R_{15}$ is chosen from a hydrogen atom and a $C_1$-$C_4$ alkyl radical.

Among the para-aminophenols of formula (XIII) above, mention may be made, for example of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol and the acid addition salts thereof.

(IV) the ortho-aminophenols that can be used as oxidation bases herein are chosen, for example, from 2-aminophenol, 2-amino-1-hydroxy-5-methylbenzene, 2-amino-1-hydroxy-6-methylbenzene and 5-acetamido-2-aminophenol, and the acid addition salts thereof.

(V) among the heterocyclic bases that can be used as oxidation bases herein, mention may be made, for example, of pyridine derivatives, pyrimidine derivatives and pyrazole derivatives, and the acid addition salts thereof.

Among the pyridine derivatives, mention may be made, for example, of the compounds described, for example, in patents GB 1 026 978 and GB 1 153 196, the disclosures of both of which are hereby incorporated by reference, and 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives, mention may be made, for example, of the compounds described, for example, in German patent DE 2 359 399 or Japanese patents JP 88-169 571 and JP 91-10659 or patent application WO 96/15765, the disclosures of all of which are hereby incorporated by reference, such as 2,4,5,6-tetraaminopyrimidine, 4-hydroxy-2,5, 6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, the disclosure of which is hereby incorporated by reference, and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylamino-pyrazolo[1,5-a]pyrimidine and the acid addition salts thereof and the tautomeric forms thereof, when a tautomeric equilibrium exists.

Among the pyrazole derivatives, mention may be made, for example, of the compounds described in patents DE 3 843 892, DE 4 133 957 and patent applications WO 94/08969, WO 94/08970, FR-A-2 733 749 and DE 195 43 988, the disclosures of all of which are hereby incorporated by reference, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

As disclosed herein, the at least one oxidation base may be present in the composition in an amount ranging from 0.0005% to 12% by weight approximately of the total weight of the composition, and for example from 0.005% to 8% by weight approximately of this weight.

The at least one coupler that may be used herein includes those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the acid addition salts thereof.

The at least one coupler may be chosen, for example, from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and the acid addition salts thereof.

When present, the at least one coupler may be present in an amount ranging from 0.0001% to 10% by weight approximately of the total weight of the composition, and for example from 0.005% to 5% by weight approximately.

In general, the acid addition salts of the at least one oxidation base and the at least one coupler are chosen, for example, from the hydrochlorides, hydrobromides, sulphates, tartrates, lactates and acetates.

Direct Dyes

The composition disclosed herein may also comprise at least one direct dye, in addition to the oxidation dyes defined above, in order to enrich the shades with glints. The at least one direct dye may, for example, be chosen from neutral, cationic or anionic nitro dyes, azo dyes or anthraquinone dyes, in a weight proportion of from approximately 0.001% to 20%, and for example from 0.01% to 10% of the total weight of the composition.

Additional Substantiv Polymers

The composition (A) and/or the composition (B) may further comprise, for example, at least one cationic or amphoteric substantive polymer, different from the at least one associative polymer of the invention and non-silicon-based.

Cationic Substantive Polymers

As used herein, the term "cationic polymer" denotes any polymer containing cationic groups and/or groups that may be ionized into cationic groups.

The cationic substantive polymers that may be used herein may be chosen from all those already known per se as improving the cosmetic properties of the hair, i.e. especially those described in patent application EP-A-337 354 and in French patents FR-2 270 846, 2 383 660, 2 598 611, 2 470 596 and 2 519 863, the disclosures of all of which are hereby incorporated by reference.

The cationic polymers that may be used, for example, are chosen from those containing units comprising primary, secondary, tertiary and/or quaternary amine groups, which may either form part of the main polymer chain or may be borne by a side substituent directly attached thereto.

The cationic polymers used generally have a number-average molecular mass ranging from 500 to $5 \times 10^6$ approximately, and for example from $10^3$ to $3 \times 10^6$ approximately.

Among the cationic polymers those that may be mentioned, for example, may be polymers of the polyamine, polyamino amide and polyquaternary ammonium type.

These are known products. They are described for example in French patents nos. 2 505 348 and 2 542 997, the disclosures of both of which are hereby incorporated by reference. Among the polymers, mention may be made of:

(1) homopolymers or copolymers derived from acrylic or methacrylic esters or amides and comprising at least one of the units of formula (XIV), (XV), (XVI) and (XVII) below:

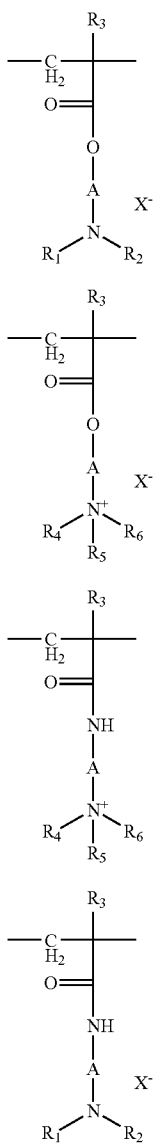

(XIV)

(XV)

(XVI)

(XVI)

wherein:
- $R_3$, which may be identical or different, is chosen from a hydrogen atom and a $CH_3$ radical;
- A, which may be identical or different, is chosen from a linear or branched alkyl group comprising 1 to 6 carbon atoms, for example 2 or 3 carbon atoms, and a hydroxyalkyl group of 1 to 4 carbon atoms;
- $R_4$, $R_5$ and $R_6$, which may be identical or different, are chosen from alkyl groups comprising from 1 to 6 carbon atoms;
- $R_1$ and $R_2$, which may be identical or different, are chosen from hydrogen and from alkyl groups comprising from 1 to 6 carbon atoms, and for example methyl or ethyl; and
- X is chosen from an anion derived from an inorganic or organic acid, such as a methosulphate anion, and a halide such as chloride or bromide.

The polymers of family (1) can also contain at least one unit derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters. Thus, among these polymers of family (1), mention may be made of:

copolymers of acrylamide and of dimethylaminoethyl methacrylate quaternized with dimethyl sulphate or with a dimethyl halide, such as the product sold under the name HERCOFLOC by the company Hercules, the copolymers of acrylamide and of methacryloyloxyethyltrimethylammonium chloride described, for example, in patent application EP-A-080 976, the disclosure of which is hereby incorporated by reference, and sold under the name BINA QUAT P 100 by the company Ciba Geigy, the copolymer of acrylamide and of methacryloyloxyethyltrimethylammonium methosulphate sold under the name RETEN by the company Hercules, quaternized or non-quaternized vinylpyrrolidone/dialkylaminoalkyl acrylate or methacrylate copolymers, such as the products sold under the name GAFQUAT by the company ISP, such as, for example, GAFQUAT 734 or GAFQUAT 755, or alternatively the products known as COPOLYMER 845, 958 and 937. These polymers are described in detail in French patents 2 077 143 and 2 393 573, the disclosures of which are hereby incorporated by reference, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold for example under the name STYLEZE CC 10 by ISP, and quaternized vinylpyrrolidone/dimethylaminopropylmethacrylamide copolymers such as the product sold under the name GAFQUAT HS 100 by the company ISP.

(2) The cellulose ether derivatives containing quaternary ammonium groups, described in French patent 1 492 597, the disclosure of which is hereby incorporated by reference, and for example polymers sold under the names JR (JR 400, JR 125 and JR 30M) or LR (LR 400 or LR 30M) by the company Union Carbide Corporation. These polymers are also defined in the CTFA dictionary as quaternary ammoniums of hydroxyethylcellulose that have reacted with an epoxide substituted with a trimethylammonium group.

(3) Cationic cellulose derivatives such as cellulose copolymers or cellulose derivatives grafted with a water-soluble monomer of quaternary ammonium, and described for example in U.S. Pat. No. 4,131,576, the disclosure of which is hereby incorporated by reference, such as hydroxyalkylcelluloses, for instance hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

The commercial products corresponding to this definition are, for example, the products sold under the names CELQUAT L 200 and CELQUAT H 100 by the company National Starch.

(4) The cationic polysaccharides described, for example, in U.S. Pat. Nos. 3,589,578 and 4,031,307, the disclosures of which are hereby incorporated by reference, such as guar gums containing cationic trialkylammonium groups. Guar gums modified with a salt (e.g., chloride) of 2,3-epoxypropyltrimethylammonium are used, for example.

Such products are sold for example under the trade names JAGUAR C13 S, JAGUAR C 15, JAGUAR C 17 or JAGUAR C162 by the company Meyhall.

(5) Polymers comprising piperazinyl units and divalent alkylene or hydroxyalkylene radicals containing straight or branched chains, optionally interrupted by oxygen, sulphur or nitrogen atoms or by aromatic or heterocyclic rings, as well as the oxidation and/or quaternization products of these polymers. Such polymers are described, for example, in French patents 2 162 025 and 2 280 361, the disclosures of both of which are hereby incorporated by reference.

(6) Water-soluble polyamino amides prepared for example by polycondensation of an acidic compound with a polyamine. These polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent may be used in proportions ranging from 0.025 to 0.35 mol per amine group of the polyamino amide. These polyamino amides may be alkylated or, if they contain at least one tertiary amine functions, they can be quaternized. Such polymers are described, for example, in French patents 2 252 840 and 2 368 508, the disclosures of which are hereby incorporated by reference.

(7) The polyamino amide derivatives resulting from the condensation of polyalkylene polyamines with polycarboxylic acids followed by alkylation with difunctional agents. Mention may be made, for example, of adipic acid/dialkylaminohydroxy-alkyldialkylenetriamine polymers in which the alkyl radical contains from 1 to 4 carbon atoms and for example is a methyl, an ethyl or a propyl. Such polymers are described for example in French patent 1 583 363, the disclosure of which is hereby incorporated by reference.

Among these derivatives, mention may be made, for example of the adipic acid/dimethylaminohydroxypropyl/diethylenetriamine polymers sold under the name CARTARETINE F, F4 or F8 by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The molar ratio between the polyalkylene polyamine and the dicarboxylic acid ranges from 0.8:1 to 1.4:1. The polyamino amide resulting therefrom is reacted with epichlorohydrin in a molar ratio of epichlorohydrin relative to the secondary amine group of the polyamino amide ranging from 0.5:1 to 1.8:1. Such polymers are described for example in U.S. Pat. Nos. 3,227,615 and 2,961,347, the disclosures of which are hereby incorporated by reference.

Polymers of this type are sold for example under the name HERCOSETT 57 by the company Hercules Inc. or alternatively under the name PD 170 or DELSETTE 101 by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (XVIII) or (XIX):

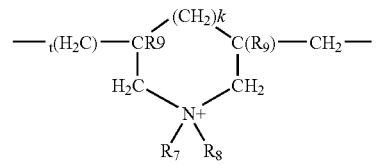

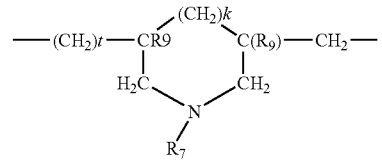

wherein:
k and t, which are identical or different, are chosen from 0 and 1, the sum k+t being equal to 1;
$R_9$ is chosen from a hydrogen atom and a methyl radical,
$R_7$ and $R_8$, independently of each other, are chosen from alkyl groups having from 1 to 6 carbon atoms, hydroxyalkyl groups in which the alkyl group for example has 1 to 5 carbon atoms, and lower $C_1$-$C_4$ amidoalkyl groups, or $R_7$ and $R_8$ can be, together with the nitrogen atom to which they are attached, heterocyclic groups such as piperidyl or morpholinyl; $R_7$ and $R_8$, independently of each other, for example, are an alkyl group having from 1 to 4 carbon atoms; and
$Y^-$ is an anion such as bromide, chloride, acetate, borate, citrate, tartrate, bisulphate, bisulphite, sulphate or phosphate.

These polymers are described for example in French patent 2 080 759 and in its Certificate of Addition 2 190 406, the disclosures of which are hereby incorporated by reference.

Among the polymers defined above, mention may be made, for example, of the dimethyldiallylammonium chloride homopolymer sold under the name MERQUAT 100 by the company Calgon (and its homologues of low weight-average molecular mass) and the copolymers of diallyldimethylammonium chloride and of acrylamide, sold under the name MERQUAT 550.

(10) The quaternary diammonium polymer containing repeating units corresponding to the formula:

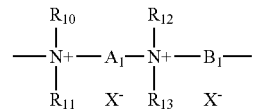

wherein:
$R_{10}$, $R_{11}$, $R_{12}$ and $R_{13}$, which may be identical or different, are chosen from aliphatic, alicyclic and arylaliphatic radicals comprising from 1 to 6 carbon atoms and from lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second heteroatom other than nitrogen, or alternatively $R_{10}$, $R_{11}$, $R_{12}$ and $R_{13}$ are chosen from linear and branched $C_1$-$C_6$ alkyl radicals substituted with at least one group chosen from nitrile, ester, acyl and amide groups and a group —CO—O—R$_{14}$-D or —CO—NH—R$_{14}$-D where R$_{14}$ is an alkylene and D is a quaternary ammonium group;

A$_1$ and B$_1$ are polymethylene groups containing from 2 to 6 carbon atoms which may be linear or branched, saturated or unsaturated, and which may contain, linked to or intercalated in the main chain, at least one aromatic ring or at least one oxygen atom, sulphur atom, or sulphoxide, sulphone, disulphide, amino, alkylamino, hydroxyl, quaternary ammonium, ureido, amide or ester groups, and X$^-$ is an anion derived from an inorganic or organic acid;

A$_1$, R$_{10}$ and R$_{12}$ can form, with the two nitrogen atoms to which they are attached, a piperazine ring. In addition, if

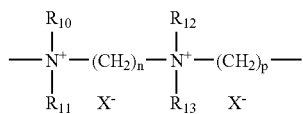

wherein R$_{10}$, R$_{11}$, R$_{12}$ and R$_{13}$, which may be identical or different, are chosen from alkyl and hydroxyalkyl radicals comprising from 1 to 4 carbon atoms, n and p are integers ranging from 2 to 20, and X$^-$ is an anion derived from an inorganic or organic acid.

(11) Polyquaternary ammonium polymers comprising repeating units of formula (XXII):

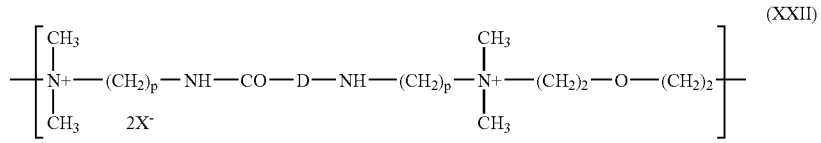

A$_1$ is a linear or branched, saturated or unsaturated alkylene or hydroxyalkylene radical, B$_1$ can also be a group —(CH$_2$)$_n$—CO-D-OC—(CH$_2$)$_n$— wherein n ranges from 1 to 100, and for example from 1 to 50, and D is chosen from:

a) a glycol residue of formula: —O-Z-O—, where Z is chosen from a linear or branched hydrocarbon-based radical and a group corresponding to one of the following formulae:

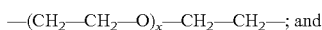

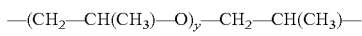

where x and y are chosen from an integer from 1 to 4, representing a defined and unique degree of polymerization and any number from 1 to 4 representing an average degree of polymerization;

b) a bis-secondary diamine residue such as a piperazine derivative;

c) a bis-primary diamine residue of formula: —NH—Y—NH—, where Y is chosen from a linear or branched hydrocarbon-based radical, and alternatively the divalent radical —CH$_2$—CH$_2$—S—S—CH$_2$—CH$_2$—; and d) a ureylene group of formula: —NH—CO—NH—.

In one embodiment, X$^-$ is an anion such as chloride or bromide.

These polymers generally have a number-average molecular mass ranging from 1000 to 100,000.

Polymers of this type are described for example in French patents 2 320 330, 2 270 846, 2 316 271, 2 336 434 and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020, the disclosures of all of which are hereby incorporated by reference.

It is, for example, possible to use polymers that comprise repeating units corresponding to the following formula (XXI):

wherein:

p is an integer ranging from 1 to 6,

D may be zero or may represent a group —(CH$_2$)$_r$—CO— in which r is a number equal to 4 or 7, and X$^-$ is an anion derived from an organic or inorganic acid.

The cationic polymers containing units of formula (XXII) are described for example in patent application EP-A-122 324 and can be prepared by the processes described in U.S. Pat. Nos. 4,157,388; 4,390,689; 4,702,906; and 4,719,282, the disclosures of all of which are hereby incorporated by reference.

In one embodiment, these polymers may have a molecular mass, measured by carbon 13 NMR, of less than 100,000, and in whose formula p is 3, and a) D is a group —(CH$_2$)$_4$—CO—, X is a chlorine atom, the molecular mass measured by carbon 13 NMR ($^{13}$C NMR) is about 5600. A polymer of this type is proposed by the company Miranol under the name MIRAPOL-AD1, b) D is a group —(CH$_2$)$_7$—CO—, X is a chlorine atom, the molecular mass measured by carbon 13 NMR ($^{13}$C NMR) is about 8100. A polymer of this type is proposed by the company Miranol under the name MIRAPOL-AZ1, c) D is zero, X is a chlorine atom, the molecular mass measured by carbon 13 NMR ($^{13}$C NMR) is about 25,500. A polymer of this type is sold by the company Miranol under the name MIRAPOL-A15, and d) a block copolymer formed of units corresponding to the polymers described in paragraphs a) and c), proposed by the company Miranol under the names MIRAPOL-9 ($^{13}$C NMR molecular mass about 7800), MIRAPOL −175 ($^{13}$C NMR molecular mass about 8000) and MIRAPOL −95 ($^{13}$C NMR molecular mass about 12,500).

In another embodiment, the polymer with units of formula (XXII) in which p is 3, D is zero, and X is a chlorine atom has the molecular mass measured by carbon 13 NMR ($^{13}$C NMR) of about 25,500.

(12) Quaternary polymers of vinylpyrrolidone and of vinylimidazole, such as, for example, the products sold under the names LUVIQUAT FC 905, FC 550 and FC 370 by the company BASF.

(13) Polyamines such as POLYQUART H sold by Henkel, which is given under the reference name "Polyethylene glycol (15) tallow polyamine" in the CTFA dictionary.

(14) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, for example methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used for example. This dispersion is sold under the name SALCARE® SC 92 by the company Allied Colloids. A crosslinked methacryloyloxyethyltrimethylammonium chloride homopolymer containing about 50% by weight of the homopolymer in mineral oil or in a liquid ester can also be used. These dispersions are sold under the names SALCARE® SC 95 and SALCARE® SC 96 by the company Allied Colloids.

Other cationic polymers which can be used in the context of the present disclosure are polyalkyleneimines, for example polyethyleneimines, polymers containing vinylpyridine or vinylpyridinium units, condensates of polyamines and of epichlorohydrin, quaternary polyureylenes and chitin derivatives.

Among all the cationic polymers which may be used, one may, for example, use the polymers of families (1), (9), (10), (11), (12) and (14), and as a further example, the polymers comprising repeating units of formulae (W) and (U) below:

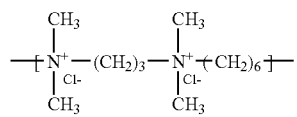

(W)

and for example those whose molecular weight, determined by gel permeation chromatography, is between 9500 and 9900;

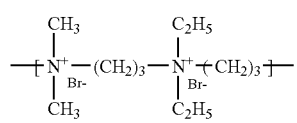

(U)

and for example those whose molecular weight, determined by gel permeation chromatography, is about 1200.

The concentration of substantive cationic polymer in the composition disclosed herein may range from 0.01% to 10% by weight relative to the total weight of the composition, for example from 0.05% to 5%, and as a further example from 0.1% to 3%.

Amphoteric Substantive Polymers

The at least one amphoteric substantive polymer that may be used herein may be chosen from polymers comprising units K and M randomly distributed in the polymer chain, wherein K is a unit derived from a monomer comprising at least one basic nitrogen atom and M is a unit derived from an acidic monomer comprising at least one carboxylic or sulphonic group, or alternatively K and M may be groups derived from zwitterionic carboxybetaine or sulphobetaine monomers.

K and M may also be a cationic polymer chain comprising primary, secondary, tertiary or quaternary amine groups, wherein at least one of the amine groups bears a carboxylic or sulphonic group linked via a hydrocarbon-based radical, or alternatively K and M form part of a chain of a polymer containing an α,β-dicarboxylic ethylene unit in which one of the carboxylic groups has been made to react with a polyamine comprising at least one primary or secondary amine group.

The at least one amphoteric polymer corresponding to the above definition may, for example, be chosen from the following polymers:

(1) polymers resulting from the copolymerization of a monomer derived from a vinyl compound bearing a carboxylic group such as, for example, acrylic acid, methacrylic acid, maleic acid, α-chloroacrylic acid, and a monomer derived from a substituted vinyl compound containing at least one basic atom, such as, for example, dialkylaminoalkyl methacrylate and acrylate, dialkylaminoalkylmethacrylamide and -acrylamide. Such compounds are described in U.S. Pat. No. 3,836,537, the disclosure of which is hereby incorporated by reference. Mention may also be made of the sodium acrylate/acrylamidopropyltrimethylammonium chloride copolymer sold under the name POLYQUART KE 3033 by the company Henkel.

The substituted vinyl compound containing at least one basic atom may also be a dialkyldiallylammonium salt such as dimethyldiallylammonium chloride. The copolymers of acrylic acid and of the latter monomer are proposed under the names MERQUAT 280, MERQUAT 295 and MERQUAT Plus 3330 by the company Calgon.

(2) Polymers containing units derived from:

a) at least one monomer chosen from acrylamides and methacrylamides substituted on the nitrogen with an alkyl radical, b) at least one acidic comonomer containing at least one reactive carboxylic group, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which may be, for example, used according to the invention are groups wherein the alkyl radicals contain from 2 to 6 carbon atoms, and for example N-ethylacrylamide, N-tert-butylacrylamide, and the corresponding methacrylamides.

The acidic comonomers are chosen, for example, from acrylic acid, methacrylic acid, crotonic acid, itaconic acid, maleic acid and fumaric acid and alkyl monoesters, having 1 to 4 carbon atoms, of maleic or fumaric acids or anhydrides.

The basic comonomers, for example, are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name AMPHOMER or LOVOCRYL 47 by the company National Starch may be, for example, used.

(3) Crosslinked and alkylated polyamino amides partially or totally derived from polyamino amides of general formula:

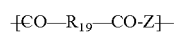

(XXIII)

wherein $R_{19}$ is chosen from a divalent radical derived from a saturated dicarboxylic acid, a mono- or dicarboxylic aliphatic acid containing an ethylenic double bond, an ester of a lower alkanol having 1 to 6 carbon atoms with these acids, and a radical derived from the addition of any one of the acids to a bis(primary) or bis(secondary) amine, and Z is chosen from a bis(primary), mono-, and bis(secondary) polyalkylene-polyamine radical and for example represents:

a) in proportions of from 60 to 100 mol %, the radical

 (XXIV)

where x=2 and p=2 or 3, or alternatively x=3 and p=2 this radical being derived from diethylenetriamine, from triethylenetetraamine or from dipropylenetriamine;

b) in proportions of from 0 to 40 mol %, the radical (XXIV) above in which x=2 and p=1 and which is derived from ethylenediamine, or the radical deriving from piperazine:

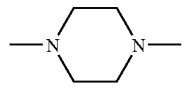

c) in proportions of from 0 to 20 mol %, the —NH—$(CH_2)_6$—NH— radical derived from hexamethylenediamine. These polyamino amines are crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are, for example, chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are, for example, chosen from propane sultone, and butane sultone. The salts of the alkylating agents are, for example, sodium or potassium salts.

(4) Polymers containing zwitterionic units of formula:

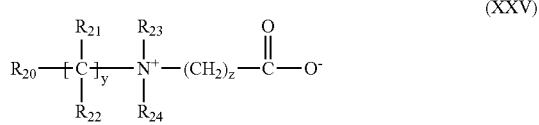 (XXV)

wherein $R_{20}$ is a polymerizable unsaturated group such as an acrylate, methacrylate, acrylamide or methacrylamide group, y and z are an integer from 1 to 3, $R_{21}$, and $R_{22}$, which are identical or different, are chosen from a hydrogen atom, methyl, ethyl, and propyl, $R_{23}$ and $R_{24}$, which are identical or different, are chosen from a hydrogen atom and alkyl radicals such that the sum of the carbon atoms in $R_{23}$ and $R_{24}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethyl-carboxymethylammonioethyl methacrylate such as the product sold under the name DIAFORMER Z301 by the company Sandoz.

(5) Polymers derived from chitosan, described for example in French patent 2137684 or U.S. Pat. No. 3,879,376, the disclosures of both of which are hereby incorporated by reference, comprising together in their chain monomer units corresponding to formulae (XXVI), (XXVII) and (XXVIII) below:

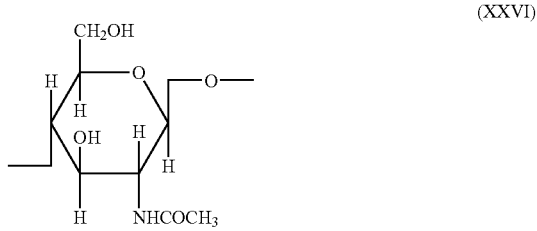 (XXVI)

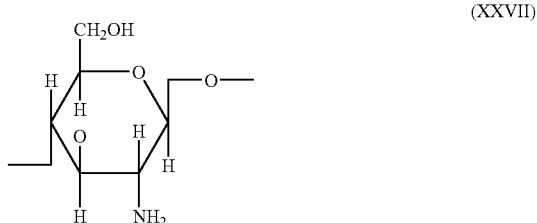 (XXVII)

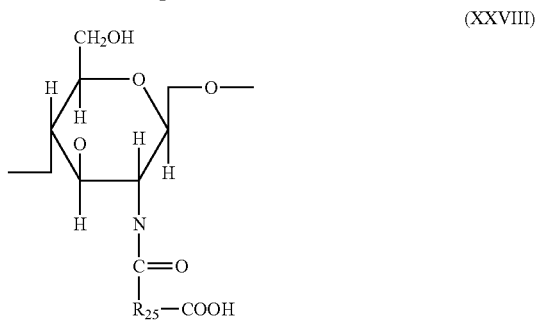 (XXVIII)

the unit (XXVI) being present in proportions ranging from 0 to 30%, the unit (XXVII) in proportions ranging from 5 to 50% and the unit (XXVIII) in proportions ranging from 30 to 90%, it being understood that, in this unit (XXVIII), $R_{25}$ represents a radical of formula:

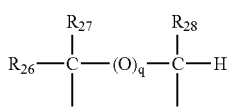

wherein q is zero or 1; if q=0, $R_{26}$, $R_{27}$ and $R_{28}$, which may be identical or different, each are chosen from a hydrogen atom, a methyl, hydroxyl, acetoxy or amino residue, a monoalkylamine residue or a dialkylamine residue which are optionally interrupted by at least one nitrogen atom and/or optionally substituted with at least one group chosen from amine, hydroxyl, carboxyl, alkylthio and sulphonic groups, and an alkylthio residue wherein the alkyl group bears an amino residue, at least one of the radicals $R_{26}$, $R_{27}$ and $R_{28}$ being, in this case, a hydrogen atom; or if q=1, $R_{26}$, $R_{27}$ and $R_{28}$ each are a hydrogen atom, as well as the salts formed by these compounds with bases or acids.

In embodiments, polymers of this type may contain from 0% to 20% by weight of units (XXVI), from 40% to 50% by weight of units (XXVII) and from 40% to 50% by weight of units (XXVIII) wherein $R_{25}$ is the radical —$CH_2$—$CH_2$—.

(6) Polymers derived from the N-carboxyalkylation of chitosan, such as N-carboxymethylchitosan or N-carboxybutylchitosan sold under the name EVALSAN by the company Jan Dekker.

(7) Polymers corresponding to the general formula (XXIX) as described, for example, in French patent 1 400 366, the disclosure of which is hereby incorporated by reference:

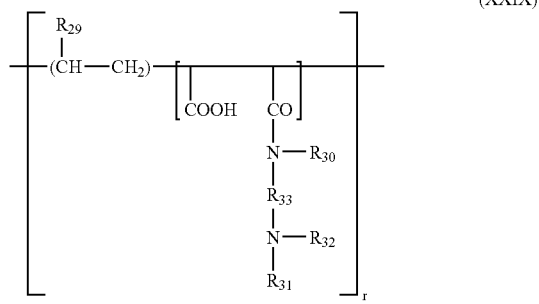

(XXIX)

wherein
$R_{29}$ is chosen from a hydrogen atom, a $CH_3O$, $CH_3CH_2O$, and a phenyl radical,
$R_{30}$ is chosen from a hydrogen and a lower alkyl radical such as methyl or ethyl,
$R_{31}$ is chosen from a hydrogen and a lower alkyl radical such as methyl or ethyl,
$R_{32}$ is chosen from a lower alkyl radical such as methyl or ethyl and a radical corresponding to the formula: —$R_{33}$—$N(R_{31})_2$, wherein $R_{33}$ is chosen from the groups —$CH_2$—$CH_2$—, —$CH_2$—$CH_2$—$CH_2$—, and —$CH_2$—$CH(CH_3)$—, $R_{31}$ having the meanings mentioned above, as well as the higher homologues of these radicals and containing up to 6 carbon atoms, wherein r is such that the molecular weight ranges from 500 to 6,000,000, and for example from 1000 and 1,000,000.

(8) Amphoteric polymers of the type —D—X—D—X— chosen from:
a) polymers obtained by the action of chloroacetic acid or sodium chloroacetate on compounds comprising at least one unit of formula:

-D-X-D-X-D-     (XXX)

wherein
D is a radical

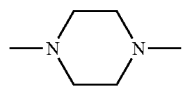

and X is chosen from the the symbol E and E', wherein E and E', which may be identical or different, are divalent radicals chosen from alkylene radicals with a straight or branched chain containing up to 7 carbon atoms in the main chain, which are unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;
b) polymers of formula:

-D-X-D-X—     (XXXI)

wherein D is a radical

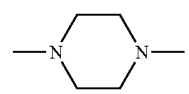

and X is chosen from the symbol E and E' and is at least once E'; E having the meaning given above and E' is a divalent radical chosen from alkylene radicals with a straight or branched chain having up to 7 carbon atoms in the main chain, which are unsubstituted or substituted with at least one hydroxyl radical and containing at least one nitrogen atom, the at least one nitrogen atom being substituted with an alkyl chain which is optionally interrupted by an oxygen atom and necessarily containing at least one carboxyl function or at least one hydroxyl function and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

In one embodiment, the at least one amphoteric polymer may be chosen from those of family (1).

In the composition disclosed herein, the at least one amphoteric polymer may be present in an amount ranging from 0.01% to 10% by weight, for example from 0.05% to 5% by weight, and as a further example from 0.1% to 3% by weight relative to the total weight of the composition.

Surfactants

The compositions disclosed herein may include at least one surfactant.

The at least one surfactant may be selected arbitrarily, alone or as mixtures, from anionic, amphoteric, non-ionic, zwitterionic and cationic surfactants.

The at least one surfactant which may be suitable is for example the following:

(i) Anionic surfactant(s):

As examples of anionic surfactants which can be used herein, alone or as mixtures, mention may be made for example (non-limiting list) of salts (for example alkali metal salts, such as sodium salts, ammonium salts, amine salts, amino alcohol salts or magnesium salts) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefinsulphonates, paraffinsulphonates; ($C_6$-$C_{24}$)alkyl sulphosuccinates, ($C_6$-$C_{24}$)alkyl ether sulphosuccinates, ($C_6$-$C_{24}$) alkylamide sulphosuccinates; ($C_6$-$C_{24}$)alkyl sulphoacetates; ($C_6$-$C_{24}$)acyl sarcosinates, and ($C_6$-$C_{24}$)acyl glutamates. It is also possible to use the carboxylic esters of $(C_6-C_{24})$alkyl polyglycosides, such as alkylglucoside citrates, alkylpolyglycoside tartrates and alkylpolyglycoside sulphosuccinates, alkylsulphosuccinamates; acyl isethionates and N-acyltaurates, the alkyl or acyl radical of all of these various compounds for example containing from 12 to 20 carbon atoms, and the aryl radical for example denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated $(C_6-C_{24})$alkyl ether carboxylic acids, polyoxyalkylenated $(C_6-C_{24})$alkyl aryl ether carboxylic acids, polyoxyalkylenated $(C_6-C_{24})$alkylamido ether carboxylic acids and their salts, for example those containing from 2 to 50 alkylene oxide, for example ethylene oxide, groups, and mixtures thereof can also be used.

(ii) Non-ionic Surfactant(s):

The non-ionic surfactants are also compounds that are well known per se (see for example in this respect M. R. Porter, "Handbook of Surfactants," Blackie & Son (Glasgow and London), pp. 116-178(1991), the disclosure of which is hereby incorporated by reference) and, as used herein, their nature is not a critical feature. Thus, they can be selected for example from (non-limiting list) polyethoxylated or polypropoxylated alkylphenols, alpha-diols or alcohols having a fatty chain containing, for example, 8 to 18 carbon atoms, it being possible for the number of ethylene oxide or propylene oxide groups to range for example from 2 to 50. Mention may also be made of copolymers of ethylene oxide and of propylene oxide, condensates of ethylene oxide and of propylene oxide with fatty alcohols; polyethoxylated fatty amides for example having from 2 to 30 mol of ethylene oxide, polyglycerolated fatty amides containing on average 1 to 5, and for example 1.5 to 4, glycerol groups; oxyethylenated fatty acid esters of sorbitan having from 2 to 30 mol of ethylene oxide; fatty acid esters of sucrose, fatty acid esters of polyethylene glycol, alkyl polyglycosides, N-alkylglucamine derivatives, amine oxides such as $(C_{10}-C_{14})$alkylamine oxides or N-acylaminopropylmorpholine oxides. Alkyl polyglycosides may be used as the non-ionic surfactants herein, for example.

(iii) Amphoteric or Zwitterionic Surfactant(s):

The amphoteric or zwitterionic surfactants, whose nature is not a critical feature herein, can be, for example (non-limiting list), aliphatic secondary or tertiary amine derivatives wherein the aliphatic radical is a linear or branched chain containing 8 to 18 carbon atoms and containing at least one water-solubilizing anionic group (for example carboxylate, sulphonate, sulphate, phosphate or phosphonate). Mention may also be made of $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives, mention may be made of the products sold under the name MIRANOL, as described in U.S. Pat. Nos. 2,528,378 and 2,781,354 and classified in the CTFA dictionary, 3rd edition, 1982, the disclosures of all of which are hereby incorporated by reference, under the names Amphocarboxyglycinates and Amphocarboxypropionates of respective structures:

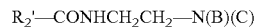

wherein: $R_2$ is a linear or branched $(C_5-C_{20})$ alkyl radical of, for example, an acid $R_2$—COOH present in hydrolysed coconut oil, a heptyl, nonyl or undecyl radical, $R_3$ is a betahydroxyethyl group, and $R_4$ is a carboxymethyl group; and

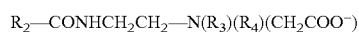

wherein: B is —$CH_2CH_2OX'$, C is —$(CH_2)_z$—Y', with z=1 or 2, X' is chosen from a —$CH_2CH_2$—COOH group and a hydrogen atom, Y' is chosen from —COOH and —$CH_2$—CHOH—$SO_3H$ radical, $R_2'$ is chosen from a linear or branched, saturated or unsaturated, $(C_5-C_{20})$ alkyl radical of an acid $R_9$—COOH present, for example, in coconut oil or in hydrolysed linseed oil, an alkyl radical, for example a $C_7$, $C_9$, $C_{11}$ or $C_{13}$ alkyl radical, a $C_{17}$ alkyl radical and its iso form, and an unsaturated $C_{17}$ radical.

These compounds are classified in the CTFA dictionary, 5th edition, 1993, the disclosure of which is hereby incorporated by reference, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name MIRANOL® C2M concentrate by the company Rhodia Chimie.

(iv) Cationic Surfactants:

Among the cationic surfactants, mention may be made for example (non-limiting list) of: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amount of the at least one surfactant present in the composition disclosed herein may range from 0.01% to 40%, and for example from 0.5% to 30% of the total weight of the composition.

Other Ingredients

The composition disclosed herein may further comprise at least one non-associative rheology modifier such as cellulosic thickeners (hydroxyethylcellulose, hydroxypropylcellulose, carboxymethylcellulose, etc.), guar gum and its derivatives (hydroxypropylguar, etc.), gums of microbial origin (xanthan gum, scleroglucan gum, etc.), and synthetic thickeners such as crosslinked homopolymers of acrylic acid or of acrylamidopropanesulphonic acid.

These supplementary thickeners may be present in an amount ranging from 0.01% to 10% by weight relative to the total weight of the composition.

The medium of the composition, which is suitable for dyeing, is, for example, an aqueous medium comprising water and may comprise cosmetically acceptable organic solvents including, for example, alcohols such as ethyl alcohol, isopropyl alcohol, benzyl alcohol and phenylethyl alcohol, or glycols or glycol ethers such as, for example, ethylene glycol monomethyl, monoethyl and monobutyl ether, propylene glycol or its ethers such as, for example, propylene glycol monomethyl ether, butylene glycol, dipropylene glycol, and also diethylene glycol alkyl ethers such as, for example, diethylene glycol monoethyl ether or monobutyl ether.

The solvents may then be present in concentrations ranging from about 0.5% to 20%, and for example from about 2% to 10% by weight, relative to the total weight of the composition.

The composition (A) may also contain an effective amount of other agents, known previously elsewhere in oxidation dyeing, such as various common adjuvants, for instance sequestrants such as EDTA and etidronic acid, UV screening agents, waxes, volatile or non-volatile, cyclic or linear or branched silicones, which are optionally organically modified (for example with amine groups), preservatives, ceramides, pseudoceramides, vegetable, mineral or synthetic oils, and vitamins or provitamins, for instance panthenol.

The composition may also contain reducing agents or antioxidants. These agents may be chosen for example from sodium sulphite, thioglycolic acid, thiolactic acid, sodium bisulphite, dehydroascorbic acid, hydroquinone, 2-methylhydroquinone, tert-butylhydroquinone, and homogentisic acid, and, in this case, they are generally present in amounts ranging from approximately 0.05% to 1.5% by weight relative to the total weight of the composition.

Needless to say, a person skilled in the art will take care to select the optional additional compound(s) mentioned above such that the properties intrinsically associated with the dye composition disclosed herein are not, or are not substantially, adversely affected by the envisaged addition(s).

In the ready-to-use composition or in the composition (B), the at least one oxidizing agent is, for example, chosen from urea peroxide, alkali metal bromates, ferricyanides, and persalts such as perborates and persulphates. In one embodiment hydrogen peroxide may be used. This oxidizing agent comprises an aqueous hydrogen peroxide solution whose titre may range, for example, from approximately 1 to 40 volumes, and as a further example from approximately 5 to 40 volumes.

Oxidizing agents that may also be used are one or more redox enzymes such as laccases, peroxidases and 2-electron oxidoreductases (such as uricase), where appropriate in the presence of their respective donor or co-factor.

The pH of the ready-to-use composition applied to the keratin fibers (composition resulting from mixing together the dye composition (A) and the oxidizing composition (B)) ranges generally from 4 to 11, for example from 6 to 10. The pH may be adjusted to the desired value using acidifying or basifying agents that are well known in the art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds of the following formula (XXXII):

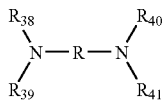

(XXXII)

wherein R is chosen from a propylene residue optionally substituted by a hydroxyl group and a $C_1$-$C_4$ alkyl radical; $R_{38}$, $R_{39}$, $R_{40}$ and $R_{41}$, which may be identical or different, are chosen from a hydrogen atom, $C_1$-$C_4$ alkyl radicals, and $C_1$-$C_4$ hydroxyalkyl radicals.

The acidifying agents are conventionally, for example, mineral or organic acids, for instance hydrochloric acid, orthophosphoric acid, carboxylic acids, for instance tartaric acid, citric acid or lactic acid, or sulphonic acids.

The dyeing process disclosed herein, for example, comprises applying the ready-to-use composition, prepared extemporaneously at the time of use from the compositions (A) and (B) described above, to wet or damp keratin fibers, leaving the composition to act for a waiting time, for example, ranging from 1 to 60 minutes, and as a further example from 10 to 45 minutes, rinsing the fibers, optionally washing them with shampoo, rinsing them again, and drying them.

One variant of this process comprises applying an above-described composition and a composition comprising at least one oxidizing agent sequentially with a time delay or simultaneously to wet or damp keratin fibers, with an optional intermediate rinse, leaving the compositions to act for an exposure time ranging from 1 to 60 minutes, rinsing the fibers, optionally washing them with shampoo, rinsing them again, and drying them.

The example which follows is intended to illustrate the invention, without, however, being limiting.

The following composition was prepared (amounts given in percentages by weight):

| | |
|---|---|
| Mixture of linear $C_{18}$ to $C_{24}$ alcohols ($C_{18}$/$C_{20}$/$C_{22}$/$C_{24}$: 7/57/30/6; alcohol content > 95%) | 3 |
| Oxyethylenated (2EO) stearyl alcohol | 4.5 |
| Oxyethylenated (21EO) stearyl alcohol | 1.75 |
| Oleic acid | 2.6 |
| Fatty-chain cationic polyurethane obtained by polycondensing 1,3-bis(isocyanatomethylcyclo-hexane), N,N-dimethylethanolamine quaternized with bromododecane, N,N-dimethylethanolamine and polyoxyethylene of molecular weight 10,000 | 0.2 |
| Crosslinked polycrylic acid (product sold under the name CARBOPOL 980 by Novéon) | 0.4 |
| Hydroxypropylmethylcellulose | 0.2 |
| Monosiopropanolamide of copra acids | 3 |
| Aminosilicone (product sold under the name SLM 28020 by Wacker) | 3 (in terms of active substance) |
| Propylene glycol | 2 |
| Sodium metabisulphite | 0.71 |
| EDTA (ethylenediaminetetraacetic acid) | 0.2 |
| Tert-butylhydroquinone | 0.3 |
| 1,4-diaminobenzene | 0.2 |
| Para-aminophenol | 1.2 |
| 1,3-dihydroxybenzene | 0.1 |
| 1-hydroxy-3-aminobenzene | 0.2 |
| 1-methyl-2-hydroxy-4-β-hydroxyethylaminobenzene | 0.8 |
| Monoethanolamine | 1 |
| Aqueous ammonia containing 20% $NH_3$ | 11 |
| Perfume q.s. | |
| Demineralized water q.s. | 100 |

The product sold under the name BELSLADM 652 by Wacker or DC2-8 299 by Dow Corning may also be used as aminosilicone.

This composition was mixed at the time of use with an oxidizing composition in the form of an emulsion containing as oxidizing agent 7.5% of hydrogen peroxide, in a proportion of 1 part by weight of dye composition per 1.5 parts by weight of oxidizing composition. The resulting mixture was applied to locks of natural hair containing 90% white hairs and was left to act for 30 minutes. After rinsing, washing with shampoo and drying, hair was obtained which was dyed in a sustained coppery red light chestnut shade.

What is claimed is:

1. A composition for the oxidation dyeing of keratin fibers comprising, in a medium suitable for dyeing:
    a) at least one oxidation dye,
    b) at least one cationic associative polymer comprising at least one fatty chain and chosen from:
        (i) quaternized celluloses modified with groups comprising at least one fatty chain,
        (ii) quaternized hydroxyethylcelluloses modified with groups comprising at least one fatty chain, and
        (iii) cationic polyurethanes; and
    c) at least one aminosilicone,
wherein the weight ratio of the at least one aminosilicone to the at least one associative polymer is greater than or equal to 1.

2. The composition according to claim 1, wherein the keratin fibers are human keratin fibers.

3. The composition according to claim 2, wherein the human keratin fibers are hair.

4. The composition according to claim 1, wherein the at least one aminosilicone is chosen from aminosilicones of formula (I), (II) and (III) below:

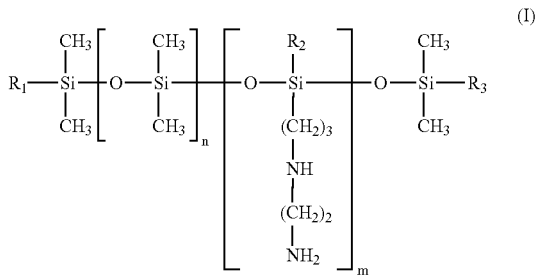

wherein in formula (I):
m and n are numbers such that the sum (n+m) may vary from 1 to 1,000, it being possible for n to be a number from 0 to 999 and for m to be a number from 1 to 1,000; and
$R_1$, $R_2$ and $R_3$, which are identical or different, are chosen from a hydroxyl radical and from $C_1$-$C_4$ alkoxy radicals, wherein at least one of the radicals $R_1$ to $R_3$ is an alkoxy radical;

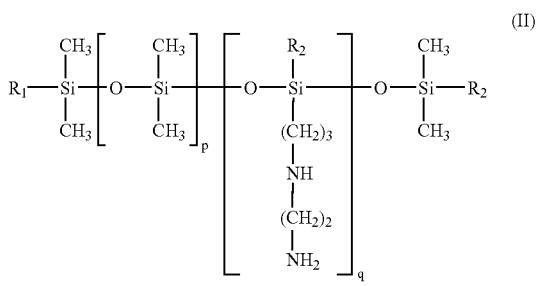

wherein in formula (II):
p and q are numbers such that the sum (p+q) may vary from 1 to 1,000, it being possible for p to be a number from 0 to 999 and for q to be a number from 1 to 1,000;

$R_1$ and $R_2$, which are different, are chosen from a hydroxyl radical and from $C_1$-$C_4$ alkoxy radicals, wherein at least one of the radicals, $R_1$ or $R_2$, is an alkoxy radical;

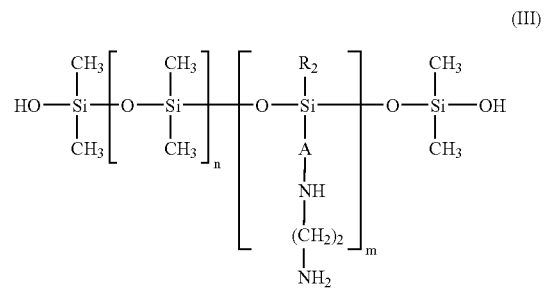

wherein in formula (III):
A is a linear or branched $C_4$-$C_8$ alkylene radical,
m and n are numbers such that the sum (n+m) may vary from 1 to 2,000, it being possible for n to be a number ranging from 0 to 1999 and for m to be a number ranging from 1 to 2,000.

5. The composition according to claim 4, wherein in formula (I) the sum (n+m) ranges from from 50 to 250, it being possible for n to be a number from 49 to 249, and m to be a number ranging from 1 to 10;
    wherein in formula (II) the sum (p+q) may vary from 50 to 350, it being possible for p to be a number from 49 to 349, and q to be a number from 1 to 10; and
    wherein in formula (III) the sum (n+m) may vary from 50 to 150, it being possible for n to be a number from 49 to 149, and m to be a number from 1 to 10.

6. The composition according to claim 4, wherein in formula (I) the sum (n+m) ranges from from 100 to 200, it being possible for n to be a number from 125 to 175, and m to be a number ranging from 1 to 5; and
    wherein in formula (II) the sum (p+q) may vary from 150 to 250, it being possible for p to be a number from 159 to 239, and q to be a number from 1 to 5.

7. The composition according to claim 4, wherein the $C_1$-$C_4$ alkoxy radical of formulae (I) and (III) is a methoxy radical.

8. The composition according to claim 4, wherein for the at least one aminosilicone of formula (I), the hydroxyl/alkoxy molar ratio ranges from 0.2:1 to 0.4:1.

9. The composition according to claim 8, wherein for the at least one aminosilicone of formula (I), the hydroxyl/alkoxy molar ratio ranges from 0.25:1 to 0.35:1.

10. The composition according to claim 9, wherein for the at least one aminosilicone of formula (I), the hydroxyl/alkoxy molar ratio is 0.3:1.

11. The composition according to claim 4, wherein for the at least one aminosilicone of formula (II), the hydroxyl/alkoxy molar ratio ranges from 1:0.8 to 1:1.1.

12. The composition according to claim 11, wherein for the at least one aminosilicone of formula (II), the hydroxyl/alkoxy molar ratio ranges from 1:0.9 to 1:1.

13. The composition according to claim 12, wherein for the at least one aminosilicone of formula (II), the hydroxyl/alkoxy molar ratio is 1:0.95.

14. The composition according to claim 4, wherein the at least one aminosilicone of formula (I) has a weight-average molecular mass ranging from 2,000 to 1,000,000.

15. The composition according to claim 14, wherein the at least one aminosilicone of formula (I) has a weight-average molecular mass ranging from 3,500 to 200,000.

16. The composition according to claim 4, wherein the at least one aminosilicone of formula (II) has a weight-average molecular mass ranging from 2,000 to 200,000.

17. The composition according to claim 16, wherein the at least one aminosilicone of formula (II) has a weight-average molecular mass ranging from 5,000 to 100,000.

18. The composition according to claim 17, wherein the at least one aminosilicone of formula (II) has a weight-average molecular mass ranging from 10,000 to 50,000.

19. The composition according to claim 4, wherein in the formula (III), A is a linear or branched $C_4$ alkylene radical.

20. The composition according to claim 4, wherein the viscosity of the at least one aminosilicone of formula (III) is greater than 25 000 mm²/s at 25° C.

21. The composition according to claim 20, wherein the viscosity of the at least one aminosilicone of formula (III) ranges from 30,000 to 200,000 mm²/s at 25° C.

22. The composition according to claim 21, wherein the viscosity of the at least one aminosilicone of formula (III) ranges from 30,000 to 150,000 mm²/s at 25° C.

23. The composition according to claim 1, wherein the at least one aminosilicone is present in the composition in an amount ranging from 0.1% to 10% by weight relative to the total weight of the composition.

24. The composition according to claim 23, wherein the at least one aminosilicone is present in the composition in an amount ranging from 0.5% to 5% by weight relative to the total weight of the composition.

25. The composition according to claim 1, wherein an alkyl group of the quaternized celluloses or hydroxyethylcelluloses contains from 8 to 30 carbon atoms.

26. The composition according to claim 1, wherein the quaternized hydroxyethylcellulose is modified with a $C_{12}$ or $C_{18}$ alkyl group resulting in a cationic amphiphilic polymer.

27. The composition according to claim 1, wherein the cationic polyurethane is a polymer of formula (IA) below:

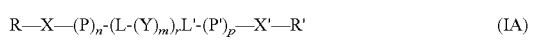

$$R—X—(P)_n\text{-}(L\text{-}(Y)_m)_r L'\text{-}(P')_p—X'—R'  \quad (IA)$$

wherein:
R and R', which may be identical or different, are chosen from a hydrophobic group and a hydrogen atom;
X and X', which may be identical or different, are chosen from a group comprising an amine function optionally bearing a hydrophobic group, and alternatively the group L';
L, L' and L", which may be identical or different, are each a group derived from a diisocyanate;
P and P', which may be identical or different, are each a group comprising an amine function optionally bearing a hydrophobic group;
Y is a hydrophilic group;
r is an integer ranging from 1 to 100, and
n, m and p each are, independently of each other, a number ranging from 0 to 1000;
wherein the molecule contains at least one protonated or quaternized amine function and at least one hydrophobic group.

28. The composition according to claim 27, wherein r is an integer ranging from 1 to 50.

29. The composition according to claim 28, wherein r is an integer ranging from 1 to 25.

30. The composition according to claim 1, wherein the at least one associative polymer is present in the composition in an amount ranging from 0.05% to 10% by weight relative to the total weight of the composition.

31. The composition according to claim 30, wherein the at least one associative polymer is present in the composition in an amount ranging from 0.1% and 5% by weight relative to the total weight of the composition.

32. The composition according to claim 1, wherein the ratio by weight of the at least one aminosilicone to the at least one associative polymer ranges from 1 to 10.

33. The composition according to claim 1, wherein the at least one oxidation dye is chosen from oxidation bases and couplers.

34. The composition according to claim 33, further comprising at least one oxidation base.

35. The composition according to claim 33, wherein the oxidation bases are chosen from ortho- and para-phenylenediamines, double bases, ortho- and para-aminophenols, heterocyclic bases, and also the acid addition salts of these compounds.

36. The composition according to claim 35, wherein the para-phenylenediamines are chosen from the compounds of formula (XI) below:

wherein:
$R_1$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical, and a $C_1$-$C_4$ alkyl radical substituted with a nitrogenous, phenyl or 4'-aminophenyl group;

$R_2$ is chosen from a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical, and a $C_1$-$C_4$ alkyl radical substituted with a nitrogenous group;

$R_1$ and $R_2$ may also form, with the nitrogen atom that bears them, a 5- or 6-membered nitrogen heterocycle optionally substituted with at least one group chosen from alkyl, hydroxyl and ureido groups;

$R_3$ is chosen from a hydrogen atom, a halogen atom, a $C_1$-$C_4$ alkyl radical, a sulpho radical, a carboxyl radical, a $C_1$-$C_4$ monohydroxyalkyl radical, a $C_1$-$C_4$ hydroxyalkoxy radical, an acetylamino$(C_1$-$C_4)$alkoxy radical, a mesylamino$(C_1$-$C_4)$alkoxy radical, and a carbamoylamino$(C_1$-$C_4)$alkoxy radical, and $R_4$ is chosen from a hydrogen atom, a halogen atom, and a $C_1$-$C_4$ alkyl radical.

37. The composition according to claim 35, wherein the double bases are chosen from the compounds of structure (XII) below:

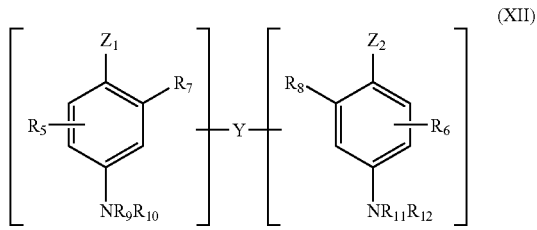

wherein:
- $Z_1$ and $Z_2$, which may be identical or different, are chosen from a hydroxyl radical, and a —$NH_2$ radical which may be substituted with at least one entity chosen from a $C_1$-$C_4$ alkyl radical and a linker arm Y;
- the linker arm Y is a linear or branched alkylene chain containing from 1 to 14 carbon atoms, which may be interrupted by or terminated with at least one nitrogenous group and/or at least one heteroatom, and optionally substituted with at least one hydroxyl or $C_1$-$C_6$ alkoxy radicals;
- $R_5$ and $R_6$, which may be identical or different, are chosen from a hydrogen atom, a halogen atom, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and a linker arm Y; and
- $R_7$, $R_8$, $R_9$, $R_{10}$, $R_{11}$ and $R_{12}$, which may be identical or different, are chosen from a hydrogen atom, a linker arm Y, and $C_1$-$C_4$ alkyl radicals;

with the proviso that the compounds of formula (XII) contain only one linker arm Y per molecule.

38. The composition according to claim 35, wherein the para-aminophenols are chosen from the compounds of structure (XIII) below:

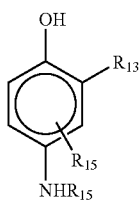

wherein:
- $R_{13}$ is chosen from a hydrogen atom, a halogen atom, a $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl, and a hydroxy($C_1$-$C_4$) alkylamino($C_1$-$C_4$)alkyl radical,
- $R_{14}$ is chosen from a hydrogen atom, a halogen atom, a $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl, and a ($C_1$-$C_4$)alkoxy($C_1$-$C_4$)alkyl radical, and
- $R_{15}$ is chosen from a hydrogen atom and a $C_1$-$C_4$ alkyl radical.

39. The composition according to claim 35, wherein the heterocyclic bases are chosen from pyridine derivatives, pyrimidine derivatives, and pyrazole derivatives.

40. The composition according to claim 33, wherein the oxidation bases are present in the composition in an amount ranging from 0.0005% to 12% by weight relative to the total weight of the composition.

41. The composition according to claim 40, wherein the oxidation bases are present in the composition in an amount ranging from 0.005% to 8% by weight relative to the total weight of the composition.

42. The composition according to claim 33, wherein the couplers are chosen from meta-phenylenediamines, meta-aminophenols, meta-diphenols, heterocyclic couplers, and the acid addition salts thereof.

43. The composition according to claim 33, wherein the couplers are present in the composition in an amount ranging from 0.0001% to 10% by weight relative to the total weight of the composition.

44. The composition according to claim 43, wherein the couplers are present in the composition in an amount ranging from 0.005% to 5% by weight relative to the total weight of the composition.

45. The composition according to claim 35, wherein the acid addition salts of the oxidation bases are chosen from hydrochlorides, hydrobromides, sulphates, tartrates, lactates and acetates.

46. The composition according to claim 42, wherein the acid addition salts of the couplers are chosen from hydrochlorides, hydrobromides, sulphates, tartrates, lactates and acetates.

47. The composition according to claim 1, further comprising at least one direct dye.

48. The composition according to claim 1, further comprising at least one amphoteric or cationic substantive non-silicon based polymer different from the claimed at least one associative polymer.

49. The composition according to claim 48, wherein the at least one substantive polymer is the homopolymer of dimethyldiallylammonium chloride.

50. The composition according to claim 48, wherein the at least one substantive polymer is a polymer of quaternary polyammonium comprising repeating units corresponding to formula (W) below:

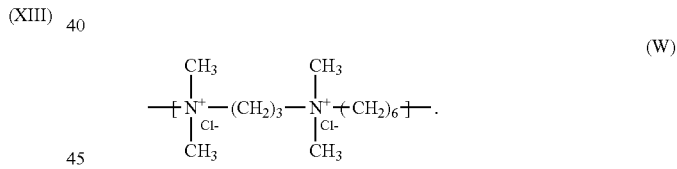

51. The composition according to claim 48, wherein the at least one substantive polymer is a polymer of quaternary polyammonium comprising repeating units corresponding to formula (U) below:

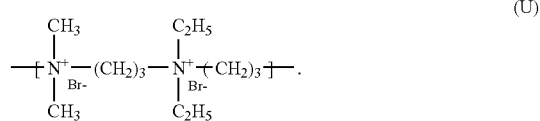

52. The composition according to claim 48, wherein the at least one cationic or amphoteric substantive polymer is present in the composition in an amount ranging from 0.01% to 10% by weight of the total weight of the composition.

53. The composition according to claim 52, wherein the at least one cationic or amphoteric substantive polymer is present in the composition in an amount ranging from 0.05% to 5% by weight of the total weight of the composition.

54. The composition according to claim 53, wherein the at least one cationic or amphoteric substantive polymer is present in the composition in an amount ranging from 0.1% to 3% by weight of the total weight of the composition.

55. The composition according to claim 1, further comprising at least one surfactant chosen from anionic, amphoteric, non-ionic, zwitterionic, and cationic su rfactants.

56. The composition according to claim 55, wherein the at least one surfactant is non-ionic.

57. The composition according to claim 55, wherein the at least one surfactant is present in the composition in an amount ranging from 0.01% to 40% by weight relative to the total weight of the composition.

58. The composition according to claim 57, wherein the at least one surfactant is present in the composition in an amount ranging from 0.5% to 30% by weight relative to the total weight of the composition.

59. The composition according to claim 1, further comprising at least one thickener.

60. The composition according to claim 59, wherein the at least one thickener is chosen from a cellulosic thickener, a guar gum derivative, a gum of microbial origin, and a synthetic thickener.

61. The composition according to claim 59, wherein the at least one thickener is present in the composition in an amount ranging from 0.01% to 10% by weight relative to the total weight of the composition.

62. The composition according to claim 1, further comprising at least one reducing agent present in the composition in an amount ranging from 0.05% to 1.5% by weight relative to the total weight of the composition.

63. A ready-to-use composition comprising
a) at least one oxidation dye,
b) at least one cationic associative polymer comprising at least one fatty chain and chosen from:
(i) quaternized celluloses modified with groups comprising at least one fatty chain,
(ii) quaternized hydroxyethylcelluloses modified with groups comprising at least one fatty chain, and
(iii) cationic polyurethanes;
c) at least one aminosilicone,
wherein the at least one aminosilicone/at least one associative polymer weight ratio is greater than or equal to 1, and
d) at least one oxidizing agent.

64. The composition according to claim 63, wherein the at least one oxidizing agent is chosen from hydrogen peroxide, urea peroxide, alkali metal bromates, ferricyanides, persalts, and redox enzymes together where appropriate with the respective donor or co-factor thereof.

65. The composition according to claim 63, wherein the at least one oxidizing agent is hydrogen peroxide.

66. The composition according to claim 65, wherein the at least one oxidizing agent is an aqueous hydrogen peroxide solution whose titre ranges from 1 to 40 volumes.

67. The composition according to claim 66, wherein the composition has a pH ranging from 4 to 11.

68. A process for the oxidation dyeing of keratin fibers comprising:
(i) applying to the keratin fibers at least one composition (A) comprising, in a medium suitable for dyeing,
a) at least one oxidation dye,
b) at least one cationic associative polymer comprising at least one fatty chain and chosen from:
(i) quaternized celluloses modified with groups comprising at least one fatty chain,
(ii) quaternized hydroxyethylcelluloses modified with groups comprising at least one fatty chain, and
(iii) cationic polyurethanes; and
c) at least one aminosilicone,
wherein the weight ratio of the at least one aminosilicone to the at least one associative polymer is greater than or equal to 1;
(ii) applying to the keratin fibers at least one composition (B) comprising at least one oxidizing agent.

69. The process according to claim 68, wherein the keratin fibers are hair.

70. The process according to claim 68, comprising mixing, at the time of use, the at least one composition (A) and the at least one composition (B).

71. The process according to claim 68, wherein the at least one composition (B) is applied sequentially before or after the at least one composition (A), with or without intermediate rinsing.

72. The process according to claim 68, wherein the color of the fibers is developed at an alkaline, neutral or acidic pH.

73. A multicompartment kit comprising:
(i) a first compartment comprising at least one composition (A) comprising, in a medium suitable for dyeing,
a) at least one oxidation dye,
b) at least one cationic associative polymer comprising at least one fatty chain and chosen from:
(i) quaternized celluloses modified with groups comprising at least one fatty chain,
(ii) quaternized hydroxyethylcelluloses modified with groups comprising at least one fatty chain, and
(iii) cationic polyurethanes; and
c) at least one aminosilicone,
wherein the weight ratio of the at least one aminosilicone to the at least one associative polymer is greater than or equal to 1;
(ii) a second compartment comprising at least one composition (B) comprising at least one oxidizing agent.

74. The composition according to claim 1, wherein the ratio by weight of the at least one aminosilicone to the at least one associative polymer ranges from 1 to 5.

* * * * *

UNITED STATES PATENT AND TRADEMARK OFFICE
CERTIFICATE OF CORRECTION

PATENT NO.       : 7,410,505 B2                                      Page 1 of 2
APPLICATION NO.  : 10/728954
DATED            : August 12, 2008
INVENTOR(S)      : François Cottard et al.

It is certified that error appears in the above-identified patent and that said Letters Patent is hereby corrected as shown below:

In claim 4, column 43, lines 52-61,

"
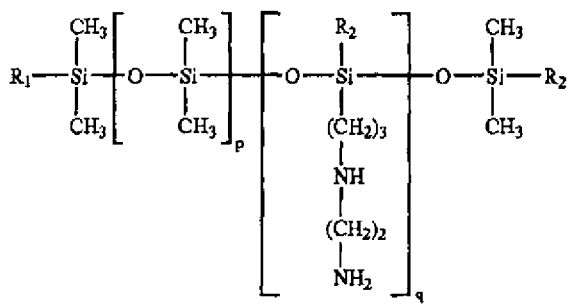
"

should read

--
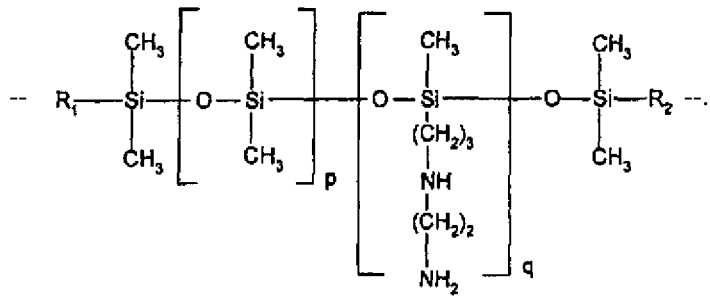
--.

In claim 4, column 44, lines 8-17,

"
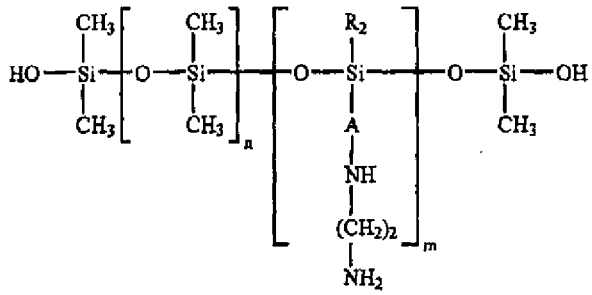
"

UNITED STATES PATENT AND TRADEMARK OFFICE
CERTIFICATE OF CORRECTION

PATENT NO. : 7,410,505 B2  
APPLICATION NO. : 10/728954  
DATED : August 12, 2008  
INVENTOR(S) : François Cottard et al.

It is certified that error appears in the above-identified patent and that said Letters Patent is hereby corrected as shown below:

should read

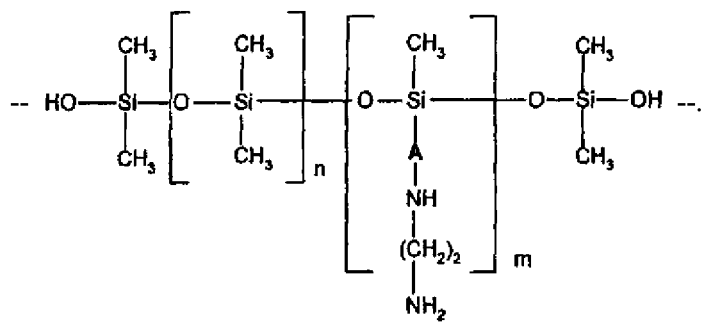

In claim 6, column 44, line 37, "ranges from from 100" should read --ranges from 100--.

In claim 7, column 44, line 45, "and (III) is" should read --and (III) is--.

In claim 20, column 45, line 17, "25 000" should read --25,000--.

In claim 27, column 45, line 41, "R-X-$(P)_n$-(L-$(Y)_m)_r$L'-$(P')_p$-X'-R'" should read --R-X-$(P)_n$-(L-$(Y)_m)_r$-L'-$(P')_p$-X'-R'--.

In claim 27, column 45, line 49, "group L';" should read --group L";--.

In claim 55, column 49, line 7, "su rfactants." should read --surfactants.--.

Signed and Sealed this

Twenty-eighth Day of October, 2008

JON W. DUDAS  
*Director of the United States Patent and Trademark Office*